(12) United States Patent
Rao et al.

(10) Patent No.: US 10,360,671 B2
(45) Date of Patent: Jul. 23, 2019

(54) TOOL HEALTH MONITORING AND MATCHING

(71) Applicant: KLA-Tencor Corporation, Milpitas, CA (US)

(72) Inventors: Ravichander Rao, Bangalore (IN); Gary Taan, San Jose, CA (US); Andreas Russ, Brooktondale, NY (US); Bjorn Brauer, Beaverton, OR (US); Roger Davis, Beaverton, OR (US); Bryant Mantiply, Mountainview, CA (US); Swati Ramanathan, Oakland, CA (US); Karen Biagini, Watsonville, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 58 days.

(21) Appl. No.: 15/646,808

(22) Filed: Jul. 11, 2017

(65) Prior Publication Data
US 2019/0019280 A1 Jan. 17, 2019

(51) Int. Cl.
G06T 7/00 (2017.01)
G01N 21/88 (2006.01)

(52) U.S. Cl.
CPC ......... G06T 7/001 (2013.01); G01N 21/8851 (2013.01); *G01N 2021/8887* (2013.01); *G06T 2207/20056* (2013.01); *G06T 2207/30148* (2013.01); *G06T 2207/30164* (2013.01)

(58) Field of Classification Search
CPC .......... G06T 7/001; G06T 2207/20056; G06T 2207/30164; G06T 2207/30148; G01N 21/8851; G01N 2021/8887
See application file for complete search history.

(56) References Cited

U.S. PATENT DOCUMENTS

| 6,483,538 | B2 | 11/2002 | Hu | |
|---|---|---|---|---|
| 6,496,958 | B1 * | 12/2002 | Ott | G06T 7/0004 257/E21.528 |
| 6,647,348 | B2 * | 11/2003 | Madge | G01R 31/2894 700/110 |
| 2002/0069024 | A1 * | 6/2002 | Dor | G06Q 30/02 702/82 |

(Continued)

FOREIGN PATENT DOCUMENTS

JP 2012018955 A 1/2012

OTHER PUBLICATIONS

ISA/KR, International Search Report for PCT/US2017/044030 dated Apr. 11, 2018.

*Primary Examiner* — Ming Y Hon

(74) *Attorney, Agent, or Firm* — Hodgson Russ LLP

(57) ABSTRACT

Systems and methods for tool health monitoring and matching through integrated real-time data collection, event prioritization, and automated determination of matched states through image analysis are disclosed. Data from the semiconductor production tools can be received in real-time. A control limit impact (CLI) of the parametric data and the defect attributes data can be determined and causation factors can be prioritized. Image analysis techniques can compare images and can be used to judge tool matching, such as by identifying one of the states at which the two or more of the semiconductor manufacturing tools match.

23 Claims, 25 Drawing Sheets

(56) References Cited

U.S. PATENT DOCUMENTS

| | | | |
|---|---|---|---|
| 2002/0155628 A1* | 10/2002 | Bulaga | H01L 22/20 |
| | | | 438/14 |
| 2003/0050761 A1* | 3/2003 | Okabe | G01N 21/95607 |
| | | | 702/82 |
| 2003/0061212 A1* | 3/2003 | Smith | G06Q 10/06 |
| 2007/0219738 A1* | 9/2007 | Weiher | G05B 19/41875 |
| | | | 702/82 |
| 2008/0075353 A1* | 3/2008 | Tek | G01N 21/4738 |
| | | | 382/145 |
| 2008/0275586 A1* | 11/2008 | Ko | G05B 23/0221 |
| | | | 700/110 |
| 2013/0006406 A1 | 1/2013 | Aharoni et al. | |
| 2014/0355867 A1* | 12/2014 | Lin | G06T 7/001 |
| | | | 382/149 |
| 2015/0346709 A1 | 12/2015 | Han et al. | |
| 2018/0113441 A1 | 4/2018 | Biagini et al. | |

\* cited by examiner

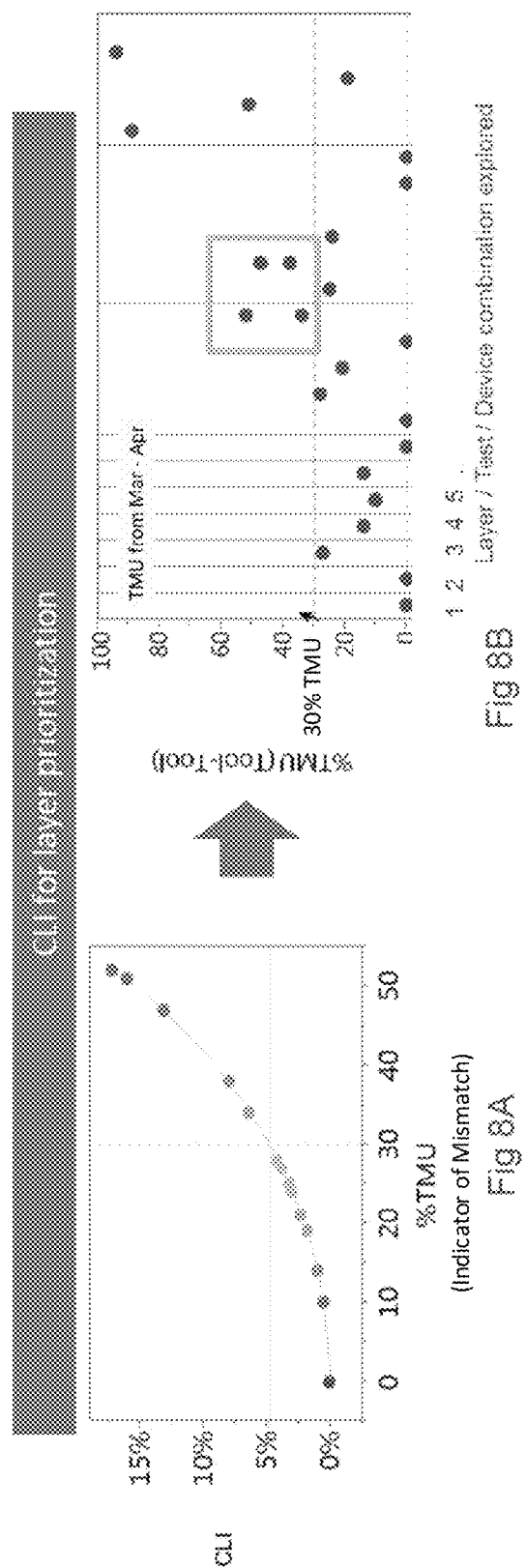

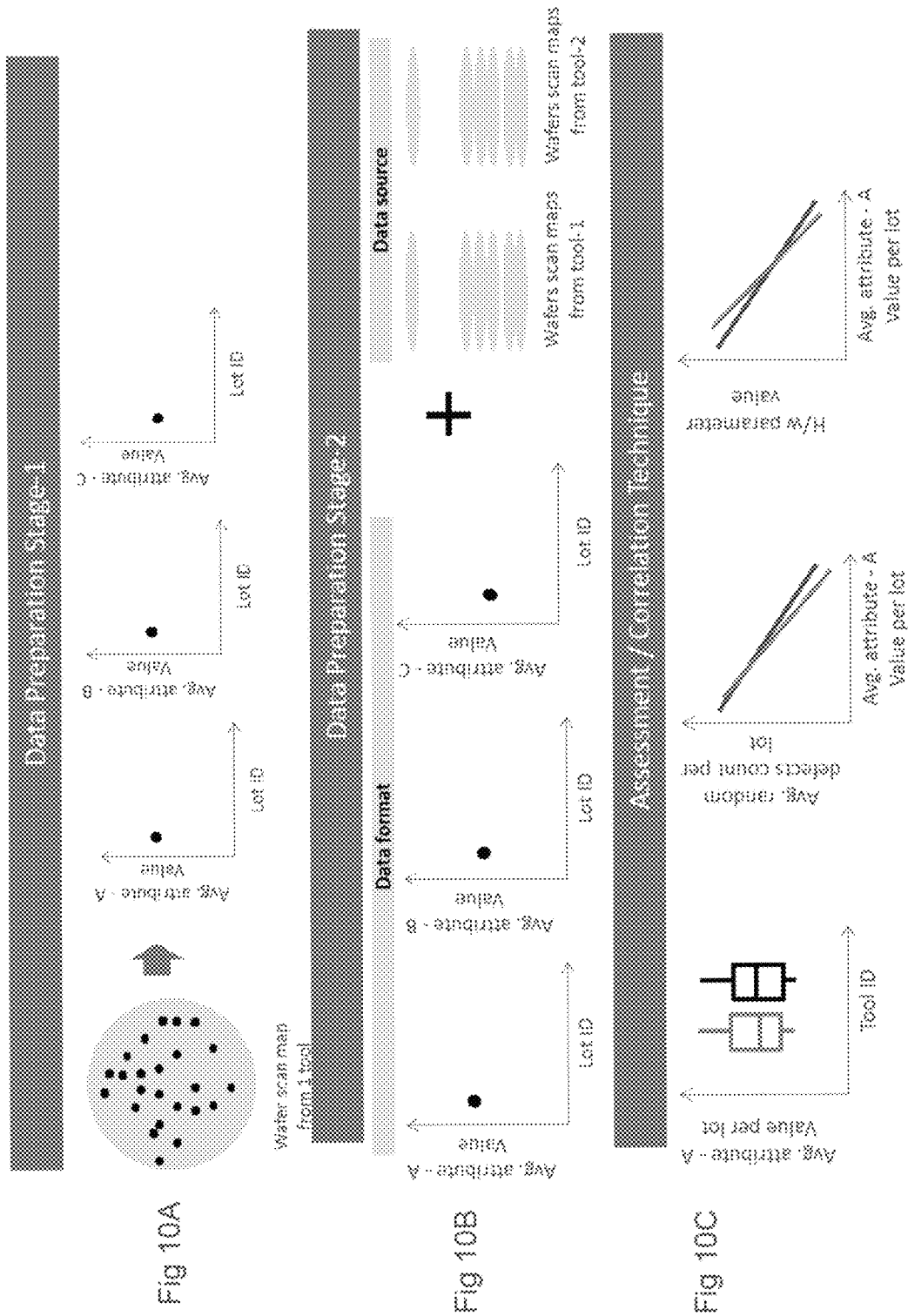

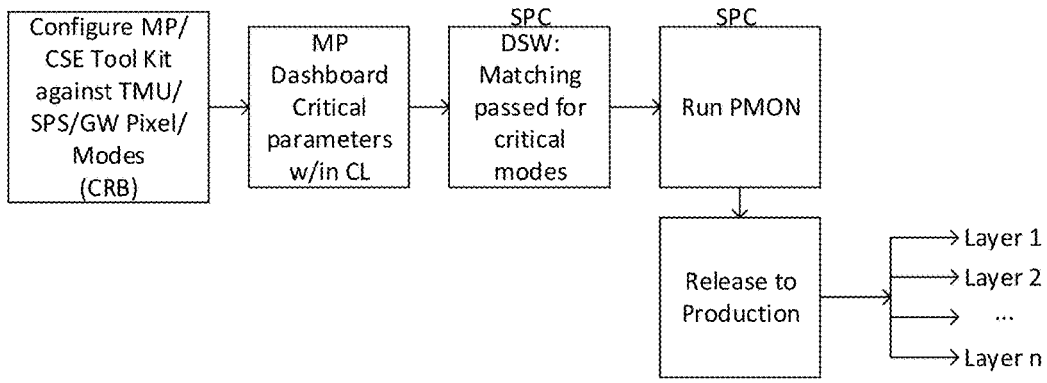
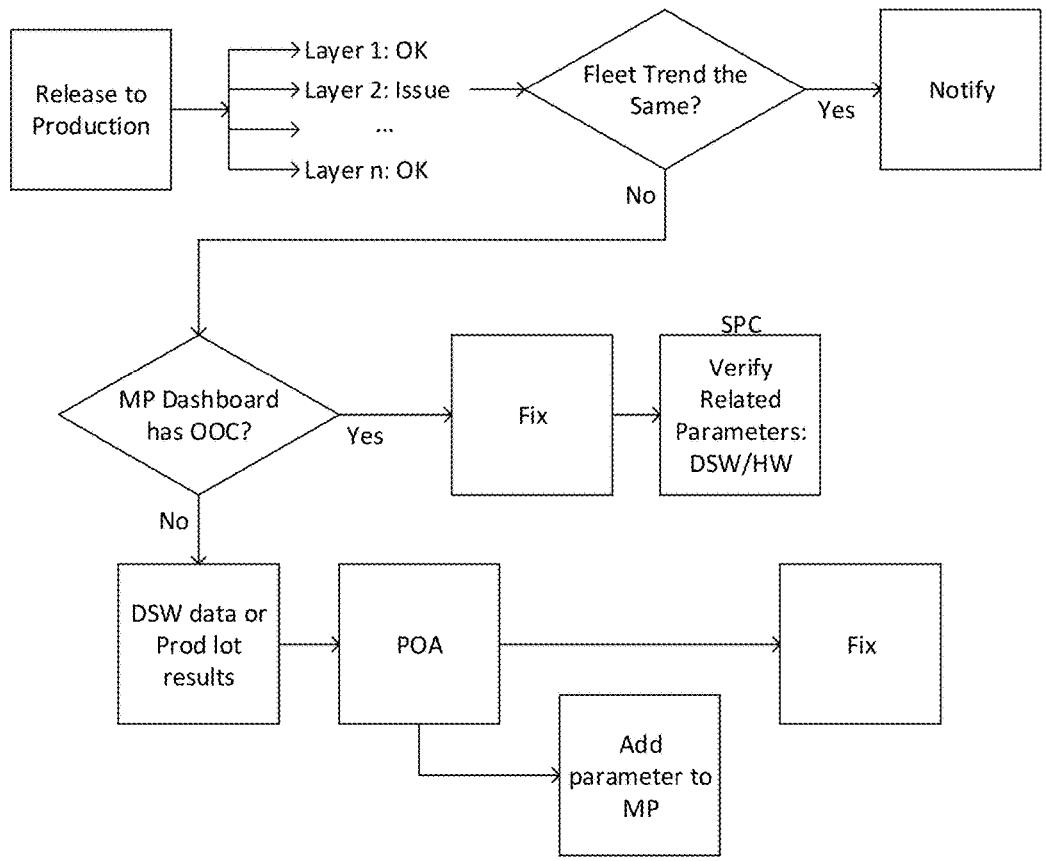
FIG. 21

TOOL HEALTH MONITORING AND MATCHING

FIELD OF THE DISCLOSURE

This disclosure relates to process control for manufacturing.

BACKGROUND OF THE DISCLOSURE

The quality of state-of-the-art products is becoming increasingly important as these products become a fundamental part of our modern, high tech economy. Manufacturers continue to focus on quality control and reproducibility to meet the demands of the high tech economy. Process control is used to produce the most consistent product properties in a manufacturing process. Quality control is essential in production lines where intricate or otherwise information-sensitive manufacturing is performed.

In complicated manufacturing environments, many variables are in flux simultaneously. While a semiconductor environment is referred to herein, the principles are general to any manufacturing environment. For example, in a semiconductor manufacturing environment, variables like the process recipe, measurement tool recipe, overall process health, measurement tool health, and other parameters are all in flux. Providing a technique to monitor tools in a manufacturing facility to ensure variation is not getting worse over time can be valuable to a manufacturer. If a shift is detected, there can be a fast response to address the detected shift.

Tool monitoring and corrective actions are done periodically in a manufacturing environment through Preventive Maintenance (PM). To capture tool drifts earlier than PMs, the PMs are complemented by monitoring standard wafers or a characterized wafer (e.g., monitor wafer or golden wafer). While the PMs attempted to calibrate the tool back into its operating range, the standard wafers attempted to identify the tool drifts that may happen between or after PMs through periodic scanning of the wafer and monitoring of the defect counts and/or monitoring of defect capture rate. If there was any drift in the production statistical process control (SPC) and/or any drift in the trend of the standard wafer, then it was assumed to be either because of a process change by the manufacturer or because of a tool drift, which in turn required a corrective action.

In an instance, defects standards wafers (DSW) and bare silicon wafers are used, optionally with a monitor wafer, for tool monitoring. These sets of wafers are used for defect capture and trending. A significant deviation from the established trend would trigger troubleshooting action to identify a root cause. If there is no significant deviation, then the tool is released to the production for inspection of the samples. If a production layer is reported to have a deviation in its trend, the standard wafer (or monitor wafer) trend is checked to verify whether there is any drift. If there is a drift in the trend of the standard wafer or monitor wafer, then a specific plan of action (POA) is issued to identify the root cause and the monitor wafer is used for further troubleshooting. If there is no trend in these wafers, multiple POAs are issued to troubleshoot the problem.

Ad-hoc fixes also may be performed to restore tool health when a tool's performance drops. For example, when a tool's performance drops below a certain desired state, which is determined either by the manufacturer on its SPC baseline or by the tool vendor through the measurements taken at the time of PM or any other ad-hoc activity, a series of data collections are performed to identify the root cause and fix the problem.

A manufacturer risks missing an excursion if the manufacturer uses a drifting tool for taking measurements. As tool architectures become more advanced, the PM cycles are becoming longer. Consequently, there is an increased risk that tool drifts will not be detected and corrected in a timely manner. Failure to quickly correct tool drifts increases the cost of ownership for a manufacturer. Furthermore, PM time is limited so that a manufacturer can maintain tool uptime targets. Yet PM schedules increase as tools become more advanced. Without adequate PM time, the risk of missing a drift between PMs increases. Hence, a scheduled PM may not comprehensively cover hardware parameters that need to be optimized frequently. Additionally, troubleshooting and fixing the problem on an ad-hoc basis means results in unscheduled tool down times because these are reactive responses. Ad-hoc troubleshooting can also take a longer time because relevant data needs to be collected to identify the root cause. This again increases the cost of operation for the manufacturer. Furthermore, methodology of using additional wafers to detect drifts between the PMs are also not fully effective, as they do not capture the breadth of production use-cases and they increase cost of ownership. There are many other ways to perform tool monitoring to prevent the drift, but each of these tool monitoring techniques suffers from drawbacks. Hence, there is a need for a methodology that monitors the tool health based on production data without causing false alarms.

Tool matching is also tightly controlled by manufacturers so that the manufacturer can balance its production lines. Mismatched tools reduce the manufacturer's operational flexibility, and are extremely time consuming to fix because of the intensive data collection and the manual to semi-manual diagnostic processes. Therefore, manufacturers attempt to match tools to have similar performance or characteristics.

Tool matching can be performed in various ways. For example, repeated measurements may be taken on a known sample. A user runs many repeats (e.g., 10 or more) on a reference tool (e.g., a golden or master tool) and on the tool which has to be sensitivity matched to the reference tool. Tool matching is achieved when both tools show a similar defect count and defect capture rate that are defined in the tool specification documents. In most cases the user only modifies the focus offset of the microscope objective. Using this technique, the percentage of common defects at different focus offsets between the master and candidate tools is noted. The point at which the common defect percentage and the count match between the master and candidate tools meet the specification or are higher is considered the best focus offsets for matching. Taking these repeated measurements is an extremely time-consuming process. It also requires extensive manual data analysis.

Images also can be manually reviewed to perform tool matching. An investigator collects images at different focus offsets and compares them manually. The images that look similar are the focus offsets at which tools are matched. However, this process is manual and can be subjective.

Histograms also can be compared to perform the tool matching. Images from the tools to be matched are converted to histograms and shapes of the histograms are compared. This technique can involve manual review, where the differences are subjectively judged. Alternately, the histogram can be converted into statistical parameters such as mode, skewness, or kurtosis and differences can be analyzed. In the case of multiple peak histograms, the statistical parameter based comparison may not be effective, because two dissimilar histograms also may have similar statistical parameters.

Tool matching also is affected by the inspection recipe quality, which is measured by Average Self Capture Rate (ASCR) and Coefficient of Variation (COV). ASCR and COV are parameters that are controlled to improve the tool-to-tool matching. ASCR is an average of capture rates of all defects which are captured in a repeated scans of the same wafer. COV is a ratio of standard deviation in the defect count to the average defects count in repeated scan of the same wafer. These are calculated by running 10× repeats on a reference wafer. A COV<5% and ASCR >75% may be set as a standard for a good quality recipe. A lower ASCR and higher COV can cause tool matching issues and/or widen the process control limit, which increases beta risk associated with the inspection.

When a recipe that does not meet these COV and ASCR requirements causes tool mismatch, the recipe is further tuned so that the tool matching can be improved. To achieve higher ASCR and lower COV, users often desensitize the recipe by increasing threshold offset to remove lower capture rate defects or by filtering out lower capture rate defects using classification and nuisance filtering techniques or by changing the inspection modes, which may suppress the lower capture rate defect detection. To achieve this, one of the 10× repeats result that was used for calculating ASCR is selected, the lower capture rate defects are identified, and removed from the scan result using the techniques described above. However, using a single scan result to eliminate the low capture results may not improve tool matching because scan-to-scan variations in the results are not compensated for. Consequently, users tend to desensitize the inspection recipes to more than required levels, which can cause the inspection recipes to miss critical defects of interest (DOIs). Users also may not change the mode to improve the ASCR because the earlier selected mode happens to be either a best known method (BKM) mode or the best mode for capturing the DOI based on the signal-to-noise ratio investigation.

Tools can be matched better if the tools are calibrated and the recipe is robust. As tools are getting better and the calibrations are getting tighter, writing and releasing robust recipes is becoming more important for tool matching. Generally, recipes attempt to attain utmost sensitivity. These high sensitivity recipes, though required to catch the critical defects, can cause mismatch. Hence, there is a need for an improved process that can be used to reduce or eliminate tool mismatch induced by the recipe quality. Previous techniques rely on releasing the recipe first and then fixing the matching issues when it arises instead of trying to proactively fix the matching issues first. Thus, tool mismatch troubleshooting becomes reactive. Tool matching causes delays in the process ramp to the customer and increases cost of tool servicing. It also is difficult to change a recipe once it is released to production.

Therefore, improved techniques for tool monitoring and matching are needed.

BRIEF SUMMARY OF THE DISCLOSURE

In a first embodiment, a system is provided. The system comprises an interface in electronic communication with a plurality of semiconductor manufacturing tools and a process control unit in electronic communication with the interface. The process control unit is configured to receive production data from the plurality of semiconductor manufacturing tools. The production data include measurements of one or more semiconductor wafers manufactured using the semiconductor manufacturing tools. The production data include parametric data and defect attributes data. The process control unit includes a control limit impact (CLI) module, a defects count identification module, a defect attributes identification module, a prioritization module, a collection module, and an image analysis module. The CLI is configured to send an alert if a CLI of the parametric data and the defect attributes data is above a specification. The defects count identification module is configured to identify a relationship between a defects count and the parametric data. The defect attributes identification module is configured to identify a relationship between at least one trend of the defect attributes data and the parametric data. The prioritization module is configured to prioritize causation factors. The collection module collects data at different states from the parametric data for two or more of the semiconductor manufacturing tools. The image analysis module is configured to identify one of the states at which the two or more of the semiconductor manufacturing tools match.

The process control unit can include a processor, an electronic data storage unit in electronic communication with the processor, and a communication port in electronic communication with the processor and the electronic data storage unit.

The process control unit can be programmed to report out-of-control hardware parameters.

The interface can be configured to receive the production data in real-time.

The system can further include a reporting module that is configured to report out-of-control hardware parameters. The out-of-control hardware parameters are determined using the parametric data and the defect attributes data.

The process control unit can be further configured to set a priority for out-of-control hardware parameters based on a CLI score. A higher CLI score can correspond to a higher priority.

The prioritization module can be configured to prioritize the causation factors based on at least one R-square score.

In an instance, the image analysis module is programmed to: convert images to Fast Fourier Transformed (FFT) images; compare two of the FFT images pixel by pixel to generate a histogram; and determine an R-square value for the histogram. A higher R-square value corresponds to improved matching.

In another instance, the image analysis module is programmed to: define representative structures; collect image data of the representative structures from two of the semiconductor manufacturing tools; and determine a value of at least one parameter such that at least some image parameters of the image data match between the two of the semiconductor manufacturing tools.

In yet another instance, the image analysis module is programmed to: determine at least two optimized hypothesis functions to predict best matching parameters between two of the semiconductor manufacturing tools; optimize a fitting parameter to minimize mean squared error; compare the hypothesis function of the two semiconductor manufacturing tools to find an offset vector of an input variable to minimize a difference between two of the hypothesis functions; and match the two semiconductor manufacturing tools by adjusting tool variables.

In a second embodiment, a method is provided. The method comprises receiving, at a process control unit, production data from a plurality of semiconductor manufacturing tools. The production data include measurements of one or more semiconductor wafers manufactured using the semiconductor manufacturing tools. The production data include parametric data and defect attributes data. A control limit impact (CLI) of the parametric data and the defect attributes data is determined using the process control unit. A relationship between a defects count and the parametric data is identified using the process control unit. A relationship between at least one trend of the defect attributes data and the parametric data is identified using the process control unit. Causation factors are prioritized using the process control unit. Using the process control unit, the parametric data is collected at different states for two or more of the semiconductor manufacturing tools. Image analysis is performed using the process control unit to identify one of the states at which the two or more of the semiconductor manufacturing tools match.

The production data can be received at the process control unit in real-time.

The method can further include reporting out-of-control hardware parameters. The out-of-control hardware parameters are determined using the parametric data and the defect attributes data.

The method can further include setting a priority for out-of-control hardware parameters based on a CLI score. A higher CLI score corresponds to a higher priority.

The method can further include monitoring the parametric data against a control limit. The control limit is defined based on manufacturing specifications or based on sigma limits.

The CLI can be measured to determine a mismatch between at least two of the semiconductor manufacturing tools. A correlation between a random defect count and the parametric data may be performed.

Prioritization of the causation factors can be based on at least one R-square score. The R-square score for each of the causation factors may be ranked.

In an instance, the image analysis includes: converting images to Fast Fourier Transformed (FFT) images; comparing two of the FFT images pixel by pixel to generate a histogram; and determining an R-square value for the histogram. A higher R-square value corresponds to improved matching.

In another instance, the image analysis includes: defining representative structures; collecting image data of the representative structures from two of the semiconductor manufacturing tools; and determining a value of at least one parameter such that at least some image parameters of the image data match between the two of the semiconductor manufacturing tools.

In yet another instance, the image analysis includes: determining at least two optimized hypothesis functions to predict best matching parameters between two of the semiconductor manufacturing tools; optimizing a fitting parameter to minimize mean squared error; comparing the hypothesis function of the two semiconductor manufacturing tools to find an offset vector of an input variable to minimize a difference between two of the hypothesis functions; and matching the two semiconductor manufacturing tools by adjusting tool variables. In this instance, the image analysis can further include: randomly selecting a first percentage of defects as a learning set, a second percentage of defects as a cross-validation set, and remainder percentage as a test set; and testing the hypothesis functions using the cross-validation set.

DESCRIPTION OF THE DRAWINGS

For a fuller understanding of the nature and objects of the disclosure, reference should be made to the following detailed description taken in conjunction with the accompanying drawings, in which:

FIGS. 8A-8B, 9A-9C, and 10A-10C illustrate an implementation of the method of FIG. 1;

FIG. 21 is a flowchart of an embodiment for tool monitoring and maintenance with real-time data collection in accordance with the present disclosure;

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Each of the steps of the method may be performed as described further herein. The methods may also include any other step(s) that can be performed by the process control unit and/or computer subsystem(s) or system(s) described herein. The steps are performed by one or more computer systems, which may be configured according to any of the embodiments described herein. In addition, the methods described above may be performed by any of the system embodiments described herein.

The embodiments disclosed herein are disclosed with respect to semiconductor manufacturing. However, the techniques disclosed herein can be applied to other manufacturing settings, including those for electronics, automobiles, chemicals, pharmaceuticals, aircraft, or biomedical devices.

Tool health monitoring and matching through integrated real-time data collection, event prioritization, and automated determination of matched states through image analysis can reduce the time to result for the tool maintenance and matching. An integrated approach of real-time data collection for identifying mismatch causation factors, prioritization of the corrective actions based on impact to production, and analysis techniques that are suitable for automation and assessing the tool matching is disclosed. The disclosed image analysis techniques compare images, such as using machine learning techniques, and can be used to judge tool matching. Time to results will be improved, which can put recipes in production earlier. Techniques disclosed herein are suitable for a Big Data application and can be implemented toward predictive and self-maintained (e.g., self-matched) tools. Real-time monitoring of the hardware parameter and its correlation to the production SPC can help to identify the tool the drifts earlier and fix them in a timelier manner.

Figure 1:
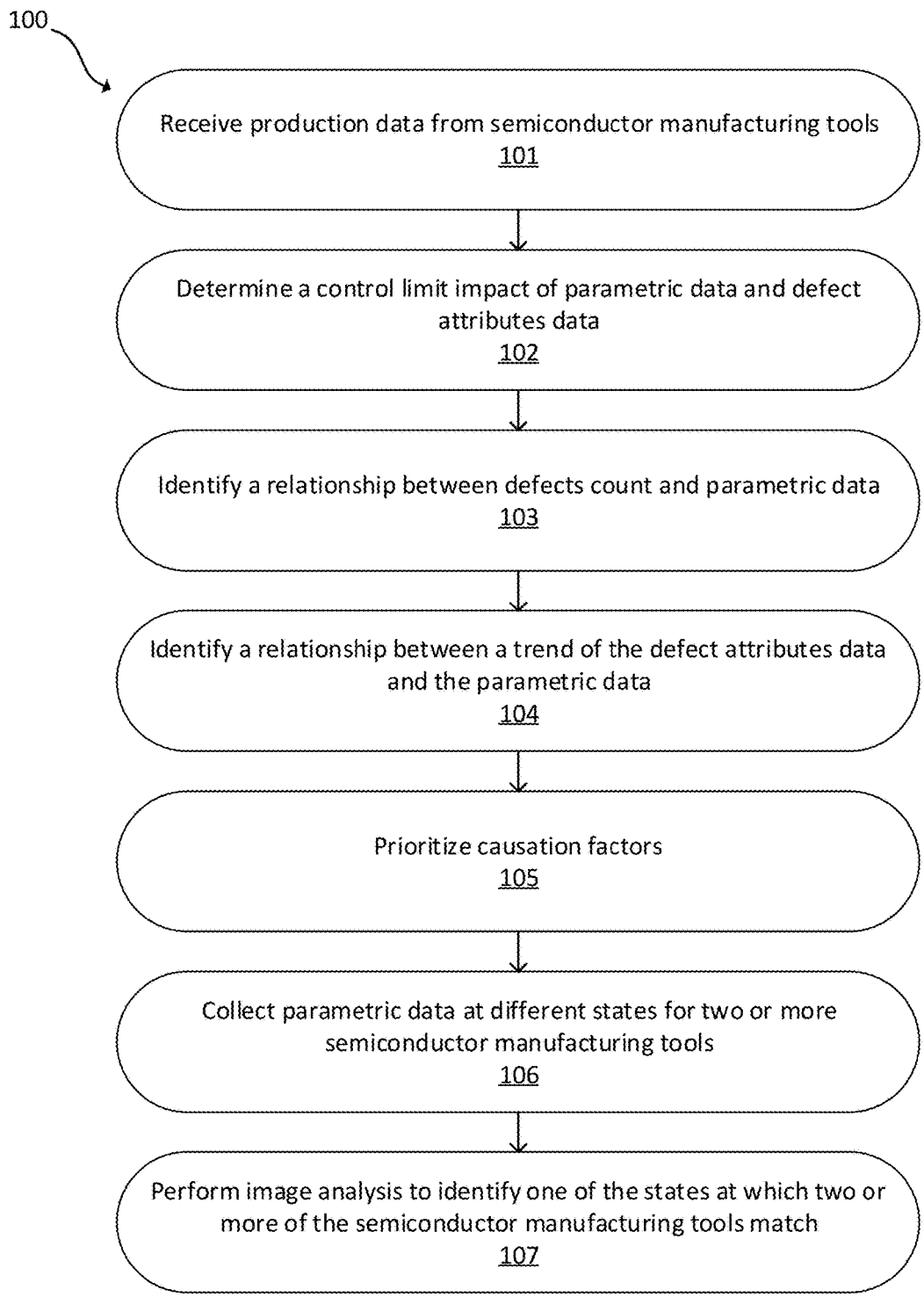
FIG. 1 is a flowchart of a method in accordance with the present disclosure.

FIG. 1 is a flowchart of a method 100. At 101, production data from a plurality of semiconductor manufacturing tools is received at a process control unit. The production data may be received at the process control unit in real-time. The production data include measurements of one or more semiconductor wafers manufactured using the manufacturing tools. The production data include parametric data and defect attributes data. Parametric data refers to any data that is related tool hardware that provides information on a state of the tool. Lamp temperature, auto focus sensor data, time delay integration (TDI) sensor data, stage speed and damping factor, and lamp life are a few examples of parametric data. Defect attribute data refers to any data that explains properties of a defect. Defect area, gray value, polarity, location of occurrence and shape are a few examples of defect attributes.

In a current implementation, frequent data collection and/or real time data collection may be performed. Real-time data collection of hardware parameters and defects attributes from the inspected wafers provides advantages over collecting data for troubleshooting after an issue is reported. The parametric data is monitored against a control limit that can be defined based on the manufacturing specifications or sigma limits identified through statistical methods. The parameters that are out of control (OOC) are reported for user intervention. A control limit impact (CLI) also may be frequently measured to gauge the tool matching. In an embodiment, no user intervention is needed, and the process control unit takes the next logical step using a machine learning algorithm.

At 102, a CLI of the parametric data and the defect attributes data can be determined using the process control unit. CLI (or total measurement uncertainty (TMU) CLI) is measured using the formula shown below.

$$TMU\ CLI = 1 - \frac{\sqrt{\sigma(\text{total process})^2 - \sigma(\text{measurement})^2}}{\sigma(\text{total process})}$$

In the above equation $\sigma$ is standard deviation in the defect counts for a particular group of sample. In the semiconductor industry, it is computed for a particular layer of a device. $\sigma$ can be generated using variance components analysis or other techniques to partition the total manufacturing process variation into the portion due to the measurement system and the portion due to other causes. Note that $\sigma$(measurement) is the term that can include both the tool-to-tool and the within-tool measurement variation. Total standard deviation of production data, $\sigma$(total process), can include both true process variation and measurement system variation. CLI measures the increase in the process control limit width due to measurement system-induced variation in the defect counts. For example, tool-tool and within-tool variation in the measurement system hardware can cause the same value to be measured differently over time. These are measurement system sources of variation. The process has many different lots or batches of material that have inherently different values of defects. Thus, lot-to-lot variation is an example of a non-measurement system source of variation. CLI metric shows the extent of tool mismatch at each measurement step in manufacturing, so it can help to prioritize hardware troubleshooting. As shown in FIGS. 8A and 8B, TMU, which is an indicator of the mismatch among the tool, is correlated to CLI. FIG. 8B shows that in a production environment, only some of the layers inspected on the tool are mismatched. The extent of the mismatch in these layers also differs. TMU and, consequently, CLI helps to identify and prioritize these mismatched layers.

CLI can also be used iteratively to indicate the tool that is causing the most mismatch, by systematically removing data from one tool at a time, and computing the change in the CLI. The tool with the largest impact to CLI is the tool with the largest impact to overall production process control.

At 103 in FIG. 1, a relationship between a defects count and the parametric data can be identified using the process control unit, such as a standard wafer or golden wafer in a semiconductor setting. When the measurement tools are matched well, the number of the defects captured by the different tools are nearly the same on the same wafer, and the hardware settings amongst the tools are similar. Additionally, the images obtained from the matched tools are alike. As a result, the defect characteristics or attributes extracted from an image of a single defect measured by different tools will not have significant difference.

However, if one of the previously matched tools has a hardware component that is shifting or degrading, then the image captured by this tool can be different compared to the image captured by the rest of the matched tools. This may manifest in a mismatch in the defect count and/or the defect attributes. Hence, a correlation study between the defect count, defect attribute, and hardware parametric data can be used to identify that a hardware shift has taken place.

In a real time matching exercise, instead of measuring a single standard or golden wafer (or sample), data from different production wafers (or samples) are inspected on different measurement tools in order to monitor process variation. Since manufacturers typically randomize the assignment of production lots to measurement tools and inspect sufficiently large number of lots, the real time trends of hardware parametric data and defect attributes can be used to gauge the tool matching.

The analysis for identifying the root cause can involve multivariate analysis using the data obtained from all the tools. A first level analysis can involve a multivariate analysis between defect count and hardware parametric data. One or more hardware parameters that exhibit high R-square score may be selected for sub-component level troubleshooting.

Figures 9A, 9B, 9C:
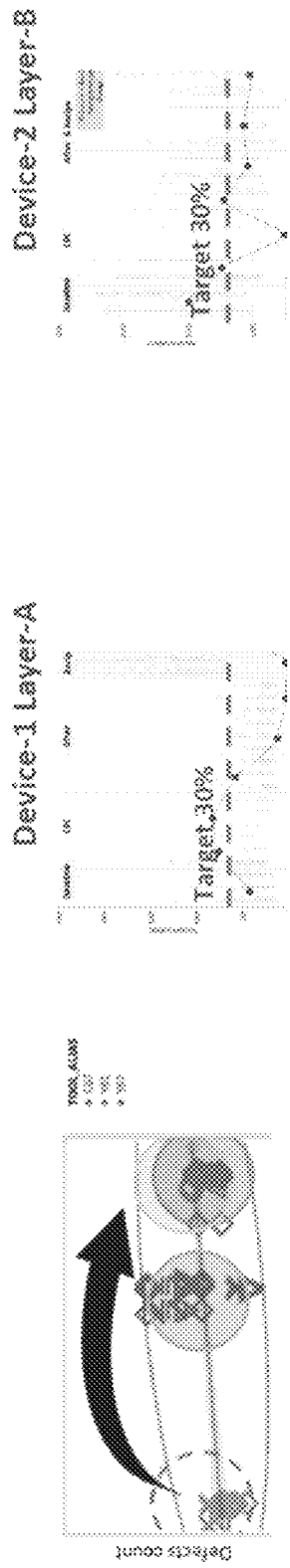

As the second level analysis, at 104 a relationship between at least one trend of the defect attributes data and the parametric data can be identified using the process control unit, and using R-square score as a metric, where R-square is a standard statistical method. This two-step approach helps to save analysis time, and also helps to narrow down the causation factor. For instance, after the first level analysis, the conclusion drawn could be a mismatch in the defect count is highly correlated to hardware parametric data that is related to the imaging system. Further, if from the second level analysis the user concludes that gray levels of the defects are strongly correlated with the imaging system and defects sizes are not correlated to the imaging system, then one can conclude that the imaging system needs to be fixed, and there is no need for adjusting the focus offset on the mismatched tool. FIG. 9A shows an example of correlation between defect counts and hardware parametric from the tools to be matched. FIG. 9B shows that after the corrective actions on the hardware parametric, the mismatched layer showed reduction in the mismatch and matched layer did not see any negative impact because of the corrective actions.

Turning back to FIG. 1, causation factors can be prioritized using the process control unit at 105. Prioritizing can be based on at least one R-square score. The R-square score for each of the causation factors can be ranked.

The parametric data can be collected at different states for two or more of the semiconductor manufacturing tools using the process control unit at 106. Once one or more causation factors are identified, changes are made to the tool that has drifted and images at suitable locations are collected on the reference wafer to perform image correlation analysis to establish the state at which the tools match. Each change made to the tool produces a unique combination of the tool setting, which is referred to as a tool state. In some instances, it may be prudent to collect data at multiple tool states to determine the state that results in the highest matching.

Image analysis can be performed at 107 using the process control unit to identify one of the states at which the two or more of the semiconductor manufacturing tools match. The causation factors that have been identified as the top reasons for causing the mismatch can be fixed through corrective actions, which may differ depending on the hardware component that needs to be fixed. However, empirically, when the tools are matched, the images captured by them are nearly identical. Hence, the impact of corrective action can be measured through automated comparison of the images through different image analysis techniques.

In an instance, the image analysis at 107 converts images to Fast Fourier Transformed (FFT) images. Two of the FFT images are compared pixel by pixel to each other. A correlation plot is generated to establish the R-square value. A higher R-square value corresponds to improved matching. This can enable automated comparison of different images.

A regular histogram based image analysis technique involves side by side comparison. The shapes of the histograms from different images can be compared, using human judgment and/or using a statistical technique which involves measuring a percentage change in the skewness, kurtosis, etc. between the two histograms. These techniques are may produce incorrect conclusion when histogram has multiple modes (peaks) and are prone to subjectivity. Some elements of these technique may still be used to complement the FFT based technique.

The image transformation (e.g., FFT) can be performed using known software, such as that provided by ImageJ. Conversion of images to FFT images can provide multiple advantages. One of the benefits is easier image alignment for comparison. Another example is that images can be cropped to a suitable size, transformed, and used for comparison. These benefits may be desired for automated analysis of large number of images because it is difficult to obtain images from the exact same coordinates with high accuracy. The transformation and use of transformed images for alignment may use techniques, such as those disclosed in U.S. Pat. No. 6,483,538, which is incorporated by reference in its entirety.

Figure 2:
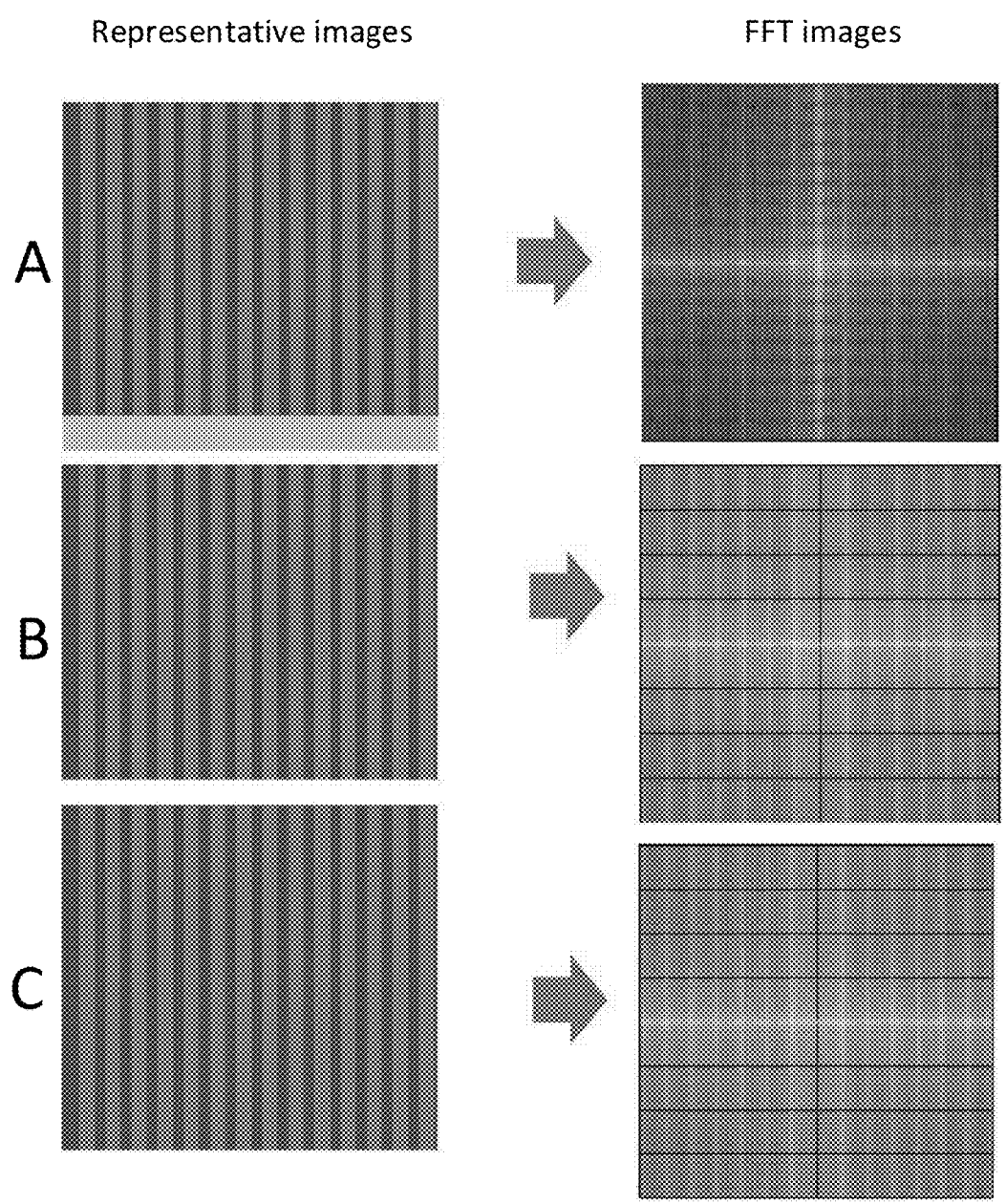
FIG. 2 illustrates a first set of three representative images (left) and corresponding FFT images (right)
Figure 3:
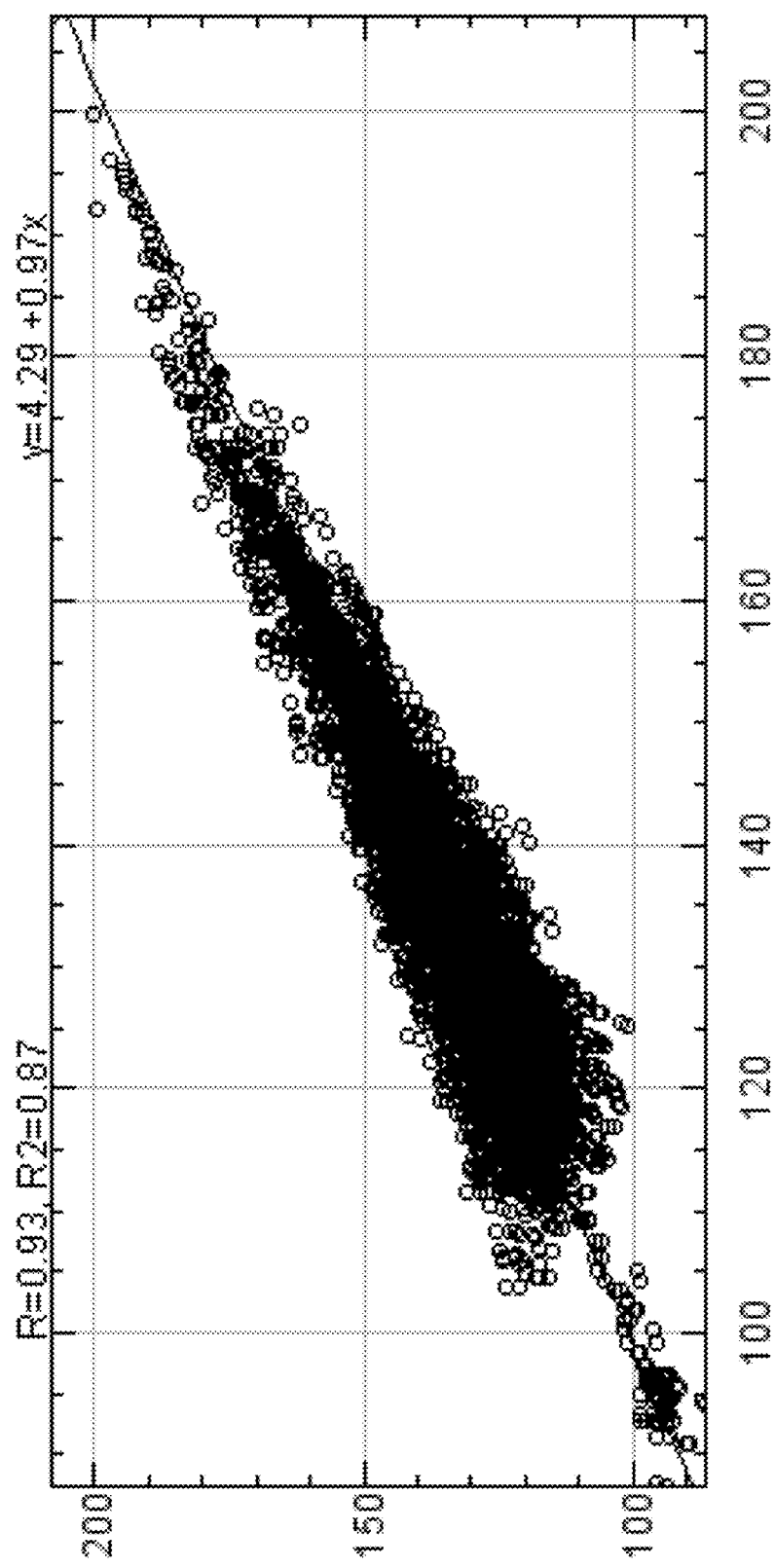
FIG. 3 is a correlation plot of images from FIG. 2.

Examples of three different representative images (left) and corresponding FFT images (right) are shown in FIG. 2. Example A in FIG. 2 is based on a semiconductor image with gray, dark, and bright patterns from a reference tool. Example B in FIG. 2 is based on a cropped images of A. Example C in FIG. 2 is based on a semiconductor image with bright and dark patterns from another tool. As shown in FIG. 2, FFT leads to an image that can have a cross hair like intersecting point in the center, which makes it easier to align the images for comparison. The effects of the minor misalignment in the images is reduced by systematic cropping. The correlation plot between Examples B and C is shown in FIG. 3.

Figure 4:
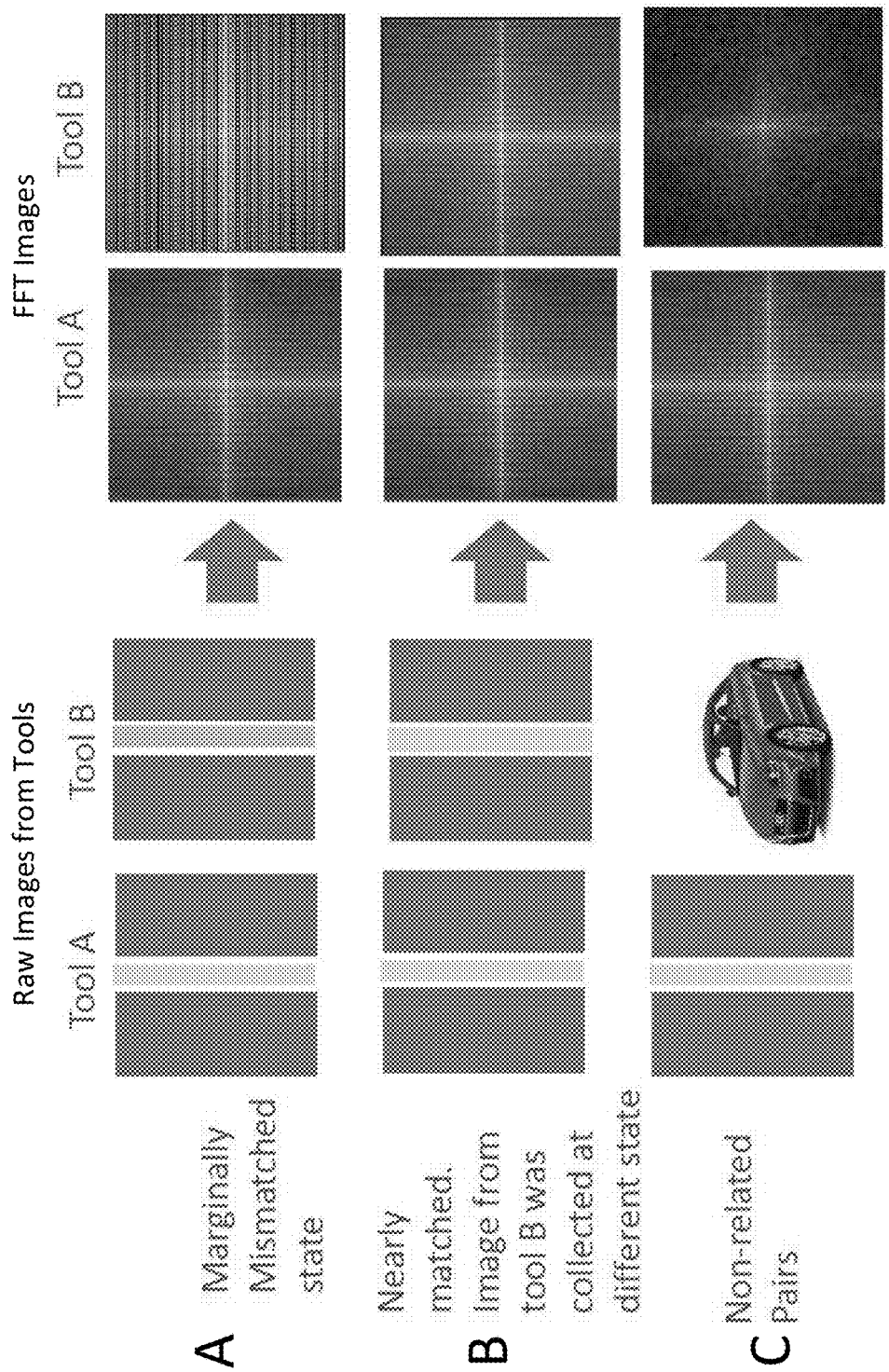
FIG. 4 shows a second sent of exemplary images and corresponding FFT images.
Figure 5:
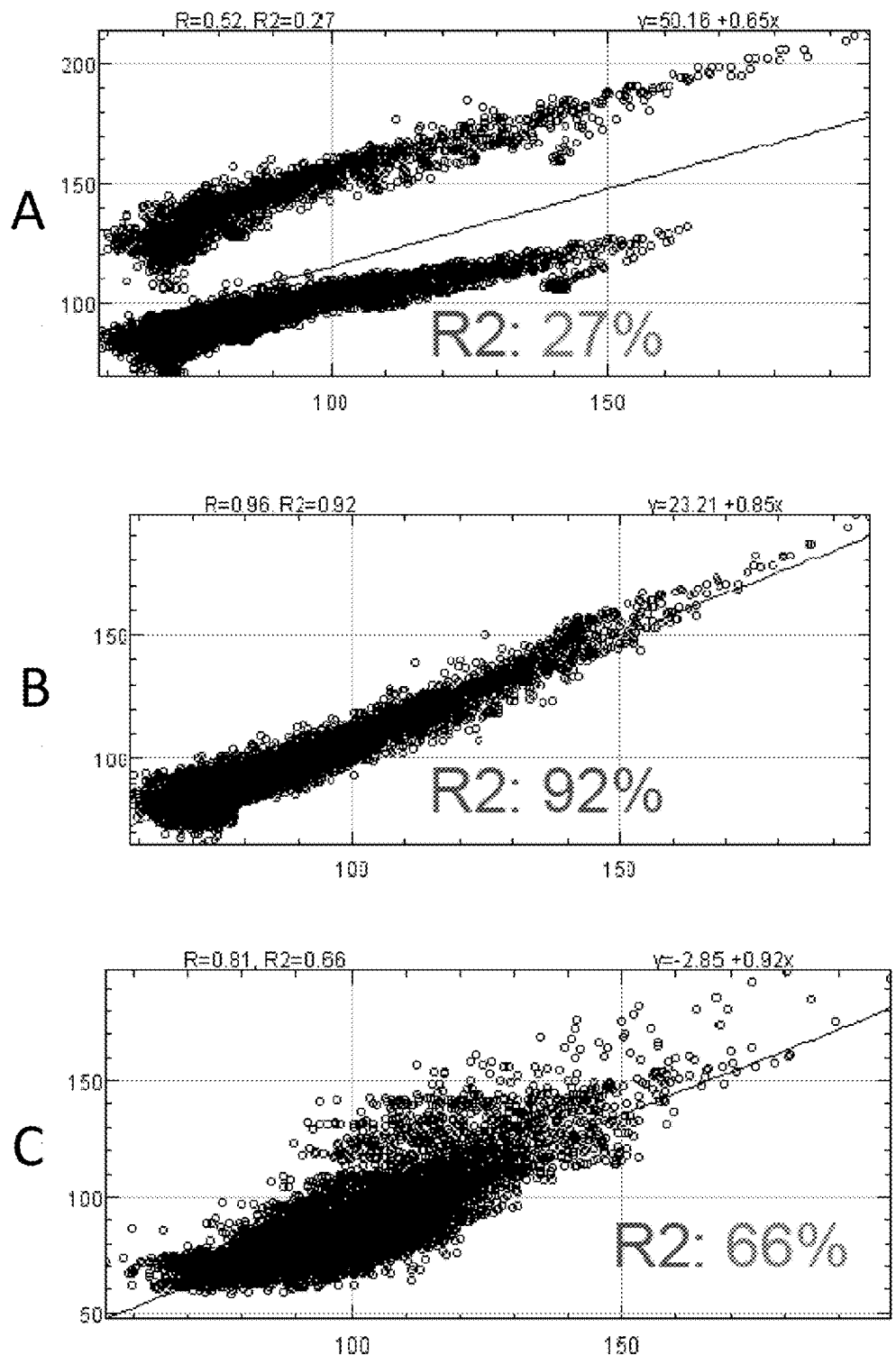
FIG. 5 includes three correlation plots of the FFT images in FIG. 4.

FIG. 4 shows a second set of exemplary images and corresponding FFT images. FIG. 5 includes three plots of the FFT images of the images shown in FIG. 4. FIG. 5A shows the correlation of FIG. 4A. FIG. 5B shows the correlation of FIG. 4B. FIG. 5C shows the correlation of FIG. 4C.

As shown in the plots of FIG. 5, R-square in FIG. 5B is higher than R-square in FIG. 5A. This is consistent with the findings of a manual review, and is the focus offset at which the tools match the best. Similarly, a comparison of the images from FIG. 4C shows a low correlation.

In another instance, the image analysis at 107 in FIG. 1, images are converted to image attributes such as gray level, contrast, or sharpness. A comparison can be done between these attributes. Image data of the representative structures can be collected from two of the semiconductor manufacturing tools. The value of at least one tool parameter can be varied on both tools. For example, the focus offset on a microscope objective can be varied on two tool. The best value of this tool parameter can be identified based on how well the image attributes match between the two of the semiconductor manufacturing tools.

During data collection, a user can define representative structures to collect simulated runtime images and calculates image attributes. The structures do not need to be at a defect location because the intent is to match attributes of the image, but not the defect. Instead of a user, an algorithm can search for representative structures based on design and collect image data or an algorithm can run a defect inspection scan on a reference tool and randomly select representative structures.

Image data for the selected sites on the reference tool are collected and the same data are collected through focus on the candidate tool. Image data also can be collected on the reference tool through focus to perform focus curve matching. The best value of matching parameter or parameters can be determined so that certain image parameters, such as image contrast, feature sharpness, of the candidate tool match those of the reference tool.

Figure 6:
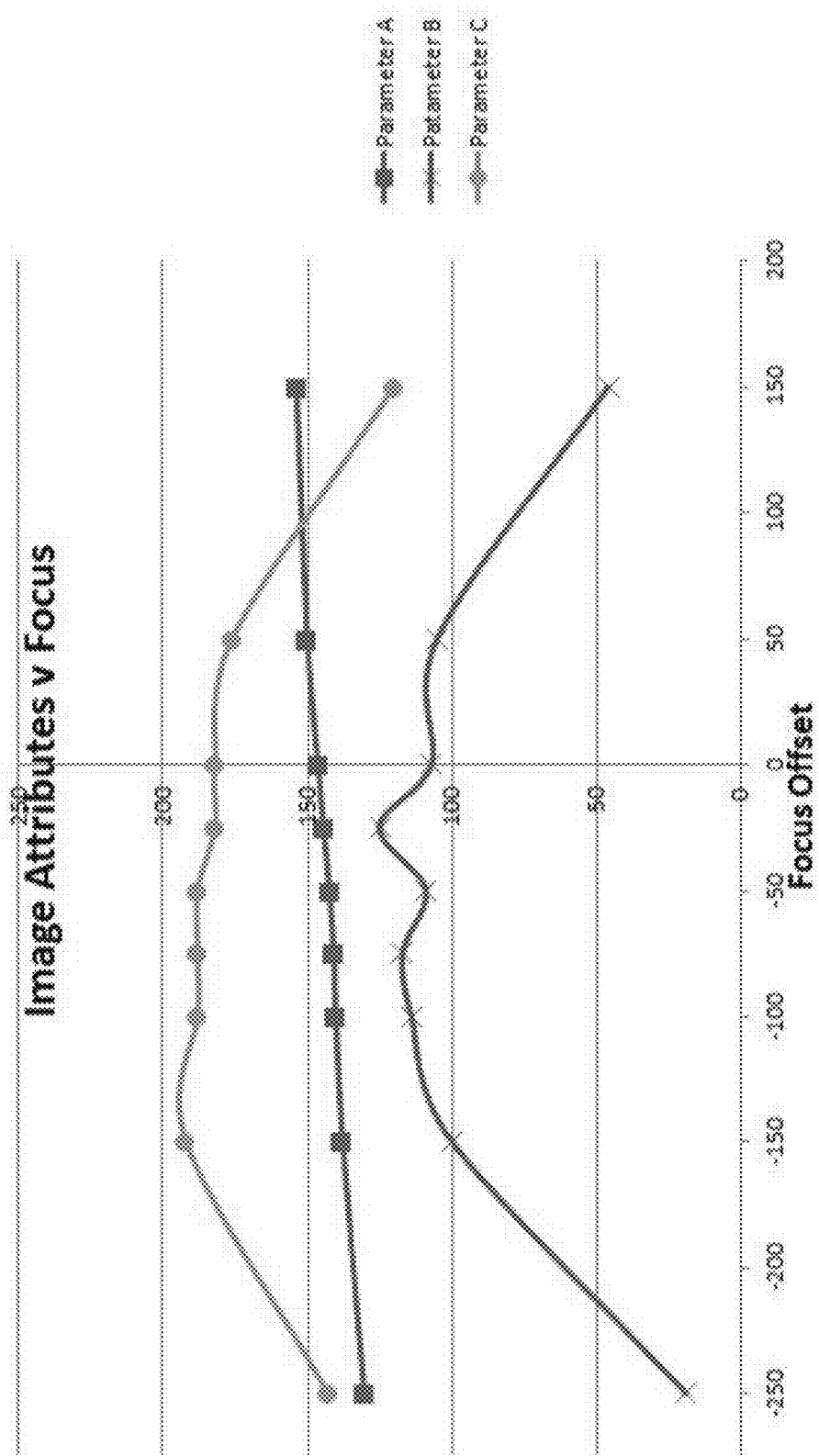
FIG. 6 is a chart showing image attributes versus focus.

The analysis technique may compare a single feature or parameter of the image collected on the candidate tool to the one on the reference tool. FIG. 6 is a chart showing image attributes versus focus. FIG. 6 illustrates the response of three derived attributes through focus.

A data fitting algorithm can then be executed to match the candidate tool response to the master tool.

For example, the feature sharpness value can be plotted for different values of a matching parameter, such as different focus offsets. The focus offset can be interpolated where, for example, the feature sharpness value matches the one from the reference tool.

In yet another instance, the image analysis at 107 in FIG. 1 determines at least two optimized hypothesis functions to predict best matching parameters between two of the semiconductor manufacturing tools. The fitting parameter θ is optimized to minimize mean squared error. The hypothesis function of the two semiconductor manufacturing tools is compared to find an offset vector of an input variable to minimize a difference between two of the hypothesis functions. The two semiconductor manufacturing tools are matched by adjusting tool variables. A first percentage of defects may be randomly selected as a learning set, a second percentage of defects may be randomly selected as a cross-validation set, and remainder percentage may be randomly selected as a test set. The hypothesis functions can be tested using the cross-validation set.

The technique for data collection may be the same as that of the previous image analysis embodiment. The analysis technique is to use advanced optimization algorithms, such as deep learning, to find best matching conditions, especially if more than just focus offset needs to be varied as shown in FIG. 7.

In an instance, a defect inspection scan is run on a reference tool. Defects are then randomly selected (e.g., 100 defects), which includes DOI, other real defects, and nuisance events across the entire inspected area. Image data is collected for all those defects on the reference and the candidate tool for different matching parameters (e.g., different focus offsets). A percentage (e.g., 60%) of defects are selected as a learning set, a percentage (e.g., 20%) as cross-validation set, and the remainder as a test set for the machine learning algorithm. The best hypothesis function or functions that can predict the best tool-to-tool matching parameters, such as the best focus offset, are found. The hypothesis function or functions are tested using the cross-validation set. The one with the lowest error or which is most reliable is found. The generalization error of the model is estimated using the test data set. If the error is low, then the hypothesis function can be used to interpolate the best value of the input variable offset vector between the reference and the candidate tool.

In an example, 60% of the defects are selected as a learning set, 20% as a cross validation set, and the remainder as test set for the machine learning algorithm. The best hypothesis function or functions that can predict the best tool-to-tool matching parameters can be performed using the following technique. $x \in \mathbb{R}^n$ is the input variable vector (e.g., focus offset). Other variables can be included to this vector as needed. $y \in \mathbb{R}^m$ is the mean of the output variable for all images including, for example, the mean/median image contrast, mean/median edge sharpness, mean/median gray level, or difference image parameters for a given input variable vector x. A machine learning hypothesis $h_\theta(x)$ is defined with the regression parameter θ. An optimization algorithm is used to optimize θ to minimize the mean squared error. The hypothesis functions of the candidate and the reference tool are compared and an offset vector $v \in \mathbb{R}^n$ of the input variable x is determined so that the difference between the two hypothesis functions is minimized. Once v is found, the candidate tool can be matched to the reference tool by adjusting the tool variables from x to x+v. The hypothesis function or functions can be tested using the cross-validation set and one can be found with the lowest error or which best predicts the focus response. If the generalization error is low, then the hypothesis function can be used to interpolate the best value of the input variable offset vector between the reference and the candidate tool.

Figure 7:
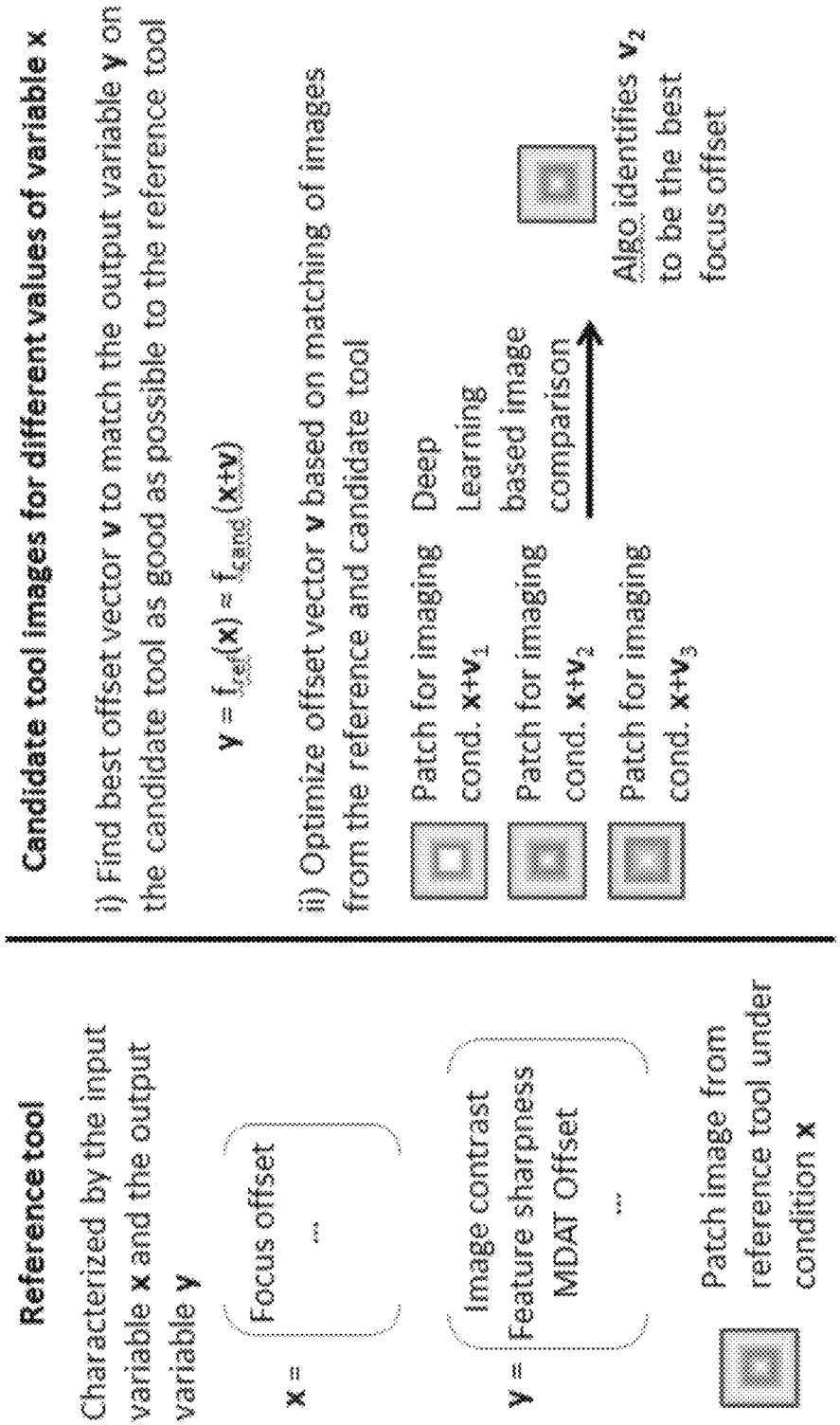
FIG. 7 illustrates an embodiment of image analysis.

In another instance of FIG. 7, deep learning (Neural Networks) are used to find the offset vector v that minimizes the difference between the images of the candidate and the reference tool for a set of randomly selected defects. In this case the Neural Network is used to derive a new attribute from the images. This attribute could for example be the output of the sigmoid or logit function that is commonly used. This new attribute is then used to find the best matching condition of the two tools.

This image analysis technique provides multiple advantages. Previously, many time-consuming repeat scans (e.g., 10 to 20) were required to do matching analysis. This image analysis technique uses images which can be collected much faster because no full wafer scans are required. The images itself can contain a statistically meaningful number of pixels, such as about 1,000 pixels each, which should not require repeats. An optimization algorithm does the data analysis and predicts the right offset vector, so no user intervention is required. Wafers with a very low defect density could not be used in the past because there was not enough statistics or one had to run a lot of repeats. With the image based matching algorithm enough statistics is collected from each image so that wafers with a very low defect density can be run.

While focus is the primary parameter to achieve matching, it is possible to add other parameters as input variable which can help to identify the reason for tool mismatches faster and make the root cause analysis more efficient.

The method 100 in FIG. 1 can report OOC hardware parameters. The OOC hardware parameters can be determined using the parametric data and the defect attributes data. Since the defect data size on each wafer varies and volume of the data processed is high, an average value of each defect attribute is taken for each wafer that is inspected, as shown in FIG. 10A. This type of dataset is prepared for each layer using the data collected on the tools to be matched, as shown in FIG. 10B. FIG. 10C, shows some of the standard techniques such as box plot analysis and correlation analysis for monitoring OOC.

Parameters that are reported OOC, but do not impact production, need not be fixed urgently. To determine the impact to production, the CLI is measured for all different layers (e.g., sample groups). The method 100 can set a priority for OOC hardware parameters based on a CLI score. If the CLI is high, then the OOC parameter may be prioritized to be fixed immediately or at a later time, the determination of which may be based on CLI score. Otherwise, the fix may be deferred to another time when the production disruption is minimum. The impact of corrective actions that are performed can be checked, such as using a dashboard that reports the tool status based on the real-time data. If the OOC is no longer reported after the corrective action, the issue may be considered fixed, and may not need additional data collection prior for releasing the tool to production.

If there is no OOC, the frequent measurement of CLI can be used to judge the tool matching status. The layers which have CLI higher than the agreed specification are considered to be mismatched. Other factors, such as recipe, environmental conditions, process, may be assumed to be non-contributing factors or may be assumed to have been addressed separately through the enforcement of the best practices. For such layers, a correlation between the random defects count and hardware parametric data may be performed. The hardware parametric data showing higher R-square score are considered to be potential causation factors, and are screened further through defect attribute and hardware correlation. Again, the R-square score is used for further narrowing down of the causation factors. The two step correlation can help to identify first the major hardware system and next the sub-system with that major hardware component that may be a causation factor. All the potential causation factors thus identified may be listed according to their R-squared value in the decreasing order. This can help prioritize the hardware corrective actions.

A user may be unable to manually review all the parameters that this technique can cover. Instead of time-consuming repeat scans that are used in traditional approaches to troubleshooting, this technique uses images that can be collected faster because no full wafer scans may be needed. The process control unit can perform the data analysis and predict the offset vector without user intervention. This technique also can use wafers with a defect density that is so low that previous techniques could not operate effectively. More parameters in the input variable also can help identify the reason for tool mismatches faster and make the root cause analysis more efficient.

This technique can be used as a predictive analysis technique. Instead of waiting for OOC to happen or a layer to exceed the CLI specification, an earlier trigger point can be set. Using that rate of degradation can be computed, the time remaining before failure or impact to CLI can be estimated, and activities can be prioritized.

Figure 11:
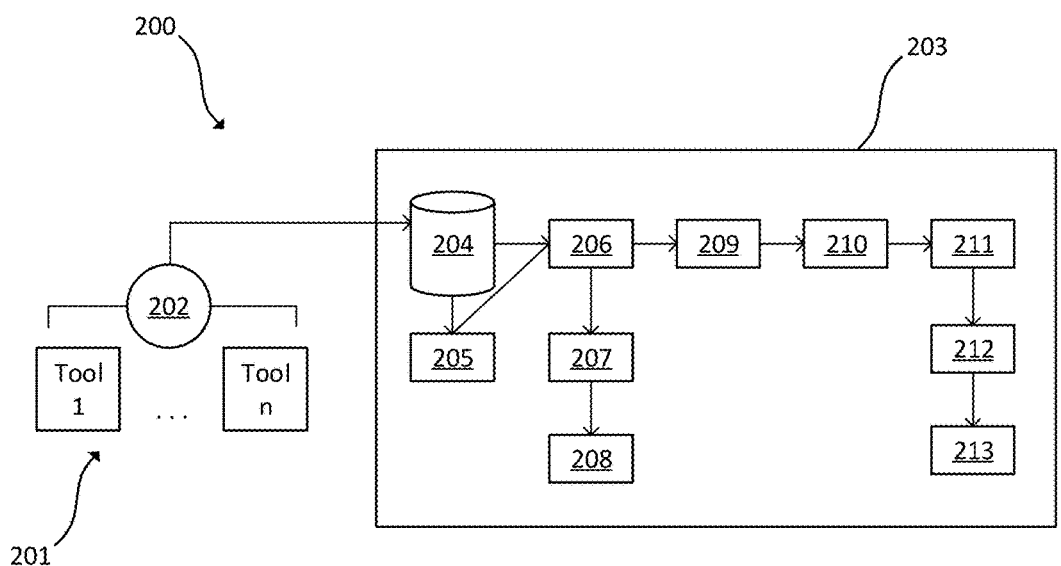
FIG. 11 is a block diagram of a system in accordance with the present disclosure.

FIG. 11 is a block diagram of an embodiment of system integration. The system 200 includes an interface 202 in electronic communication with a plurality of semiconductor manufacturing tools 201. The interface 202 may be, for example, a secured server. The interface 202 is in electronic communication with the process control unit 203. Data transfer from the semiconductor manufacturing tools 201 to the interface 202 may be frequent, such as in real-time.

Examples of the semiconductor manufacturing tools 201 include deposition tools, ion implantation tools, etching tools, lithography tools, chemical mechanical polishing tools, scanning electron microscopes, defect detection tools, defect review tools, film thickness measurement tools, surface profile measurement tools, resistivity measurement tools, overlay metrology, or critical dimension measurement tools. Other types of semiconductor manufacturing tools are possible. The semiconductor manufacturing tools 201 may be the same platform or of a similar platform. For example, the semiconductor manufacturing tools 201 may include two defect detection tools. Different manufacturing tools can be used if the manufactured devices are, for example, biomedical devices or electronics.

The process control unit 203 can have a processor, a communication port in electronic communication with the processor, and the electronic data storage unit in electronic communication with the processor and the communication port. The process control unit 203 is configured to receive production data from the semiconductor manufacturing tools 201, such as through a communication port. The production data can include measurements of one or more semiconductor wafers manufactured using the semiconductor manufacturing tools 201. The production data can include parametric data and defect attributes data.

The process control unit 203 is configured to receive production data from the semiconductor manufacturing tools 201, such as through the interface 202. The production data can relate to a device manufactured using the semiconductor manufacturing tools 201. The device may be, for example, a semiconductor wafer. The process control unit 203 can be further configured to perform the steps of the method 100 of FIG. 1.

The process control unit 203 can include a database 204 that includes hardware parametric and defects attributes. The database 204 is in electronic communication with the interface 202 and can receive information from the semiconductor manufacturing tools 201. The database 204 can store incoming data, historical data, and/or a set of reference data used for comparison.

The database 204 is in electronic communication with a reporting module 205. The reporting module 205 is programmed to report OOC hardware parameters. The OOC hardware parameters can be determined using the parametric data and the defect attributes data. The reporting module 205 may be in electronic communication with a real-time OOC reporting dashboard, CSE toolkit, MatchPoint, or other software.

The database 204 and the reporting module 205 are in electronic communication with a CLI module 206. The CLI module 206 is configured to take action, such as by sending an alert, if a CLI of the parametric data and the defect attributes data is above a specification. The CLI module 206 may act as part of a matching status check on an as-needed basis or at some set frequency.

The CLI module 206 is in electronic communication with a priority setting module 207. The priority setting module 207 is configured to set a priority for OOC hardware parameters based on a CLI score. A higher CLI score may correspond to a higher priority.

The priority setting module 207 is in electronic communication with a maintenance module 208. The maintenance module 208 is configured to perform corrective actions to fix and/or restore a baseline.

The CLI module 206 is in electronic communication with a defects count identification module 209 that is configured to identify a relationship between a defects count and parametric data. The defects count identification module 209 can identify a hardware component during tool matching.

The defects count identification module 209 is in electronic communication with a defect attributes identification module 210 that is configured to identify a relationship between at least one trend of the defect attributes data and the parametric data. The defect attributes identification module 210 can identify a hardware component and/or sub-component during tool matching.

The defect attributes identification module 210 is in electronic communication with a prioritization module 211 that is configured to prioritize causation factors. The prioritization module is configured to prioritize the causation factors based on at least one R-square score.

The prioritization module 211 is in electronic communication with a collection module 212 that collects data at different states from the parametric data for two or more of the semiconductor manufacturing tools 201. This data can be used for tool matching.

The collection module 212 is in electronic communication with an image analysis module 213 that is configured to identify one of the states at which the two or more of the semiconductor manufacturing tools 201 match. The image analysis can include one or more of image cross-correlation, image attribute versus focus offset trend match, or image attribute comparison using machine learning.

In an embodiment, the image analysis module 213 is programmed to: convert images to Fast Fourier Transformed (FFT) images; compare two of the FFT images pixel by pixel to generate a histogram; and determine an R-square value for the histogram. A higher R-square value corresponds to improved matching.

In another embodiment, the image analysis module 213 is programmed to: define representative structures; collect image data of the representative structures from two of the semiconductor manufacturing tools; and determine a value of at least one parameter such that at least some image parameters of the image data match between the two of the semiconductor manufacturing tools.

In yet another embodiment, the image analysis module 213 is programmed to: determine at least two optimized hypothesis functions to predict best matching parameters between two of the semiconductor manufacturing tools; optimize a fitting parameter to minimize mean squared error; compare the hypothesis function of the two semiconductor manufacturing tools to find an offset vector of an input variable to minimize a difference between two of the hypothesis functions; and match the two semiconductor manufacturing tools by adjusting tool variables.

Each of the modules can be executed by the processor of the process control unit 203. Instructions for each of the modules can be stored on the electronic data storage unit of the process control unit 203.

The process control unit 203 can be configured to adjust at least one of the semiconductor manufacturing tools 201 based on, for example, results of the collection module 212 or the image analysis module 213. For example, a setting on a semiconductor manufacturing tools 201 can be changed, the material input can be changed, a recipe can be changed, or a drift in a process can be addressed.

It is to be appreciated that the process control unit 203 may be implemented in practice by any combination of hardware, software, and firmware. Also, its functions as described herein may be performed by one unit, or divided up among different components, each of which may be implemented in turn by any combination of hardware, software and firmware. Program code or instructions for the process control unit 203 to implement the various methods and functions described herein may be stored in controller readable storage media, such as a memory in the electronic data storage unit, within the process control unit 203, external to the process control unit 203, or combinations thereof.

The process control unit 203 may be coupled to the components of the system 200 in any suitable manner (e.g., via one or more transmission media, which may include "wired" and/or "wireless" transmission media) such that the process control unit 203 can receive the output generated by the semiconductor manufacturing tools 201. The process control unit 203 may be configured to perform a number of functions using the output. For instance, the process control unit 203 may be configured to transmit or display results of analysis using the output. In another example, the process control unit 203 may be configured to send the output to an electronic data storage unit or another storage medium without analyzing the output. The process control unit 203 may be further configured as described herein.

The process control unit 203, other system(s), or other subsystem(s) described herein may take various forms, including a personal computer system, image computer, mainframe computer system, workstation, network appliance, internet appliance, or other device. In general, the process control unit 203 may have one or more processors that execute instructions from a memory medium. The subsystem(s) or system(s) may also include any suitable processor known in the art, such as a parallel processor. In addition, the subsystem(s) or system(s) may include a platform with high speed processing and software, either as a standalone or a networked tool.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

An additional embodiment relates to a non-transitory computer-readable medium storing program instructions executable on a process control unit or other controller for performing a computer-implemented process control method, as disclosed herein. In particular, as shown in FIG. 11, electronic data storage unit or other storage medium of the process control unit 203 may contain non-transitory computer-readable medium that includes program instructions executable on the process control unit 203. The computer-implemented method may include any step(s) of any method(s) described herein, such as those of FIG. 1.

Program instructions implementing methods such as those described herein may be stored on computer-readable medium, such as in the electronic data storage unit or other storage medium. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), SSE (Streaming SIMD Extension), or other technologies or methodologies, as desired.

Figure 23:
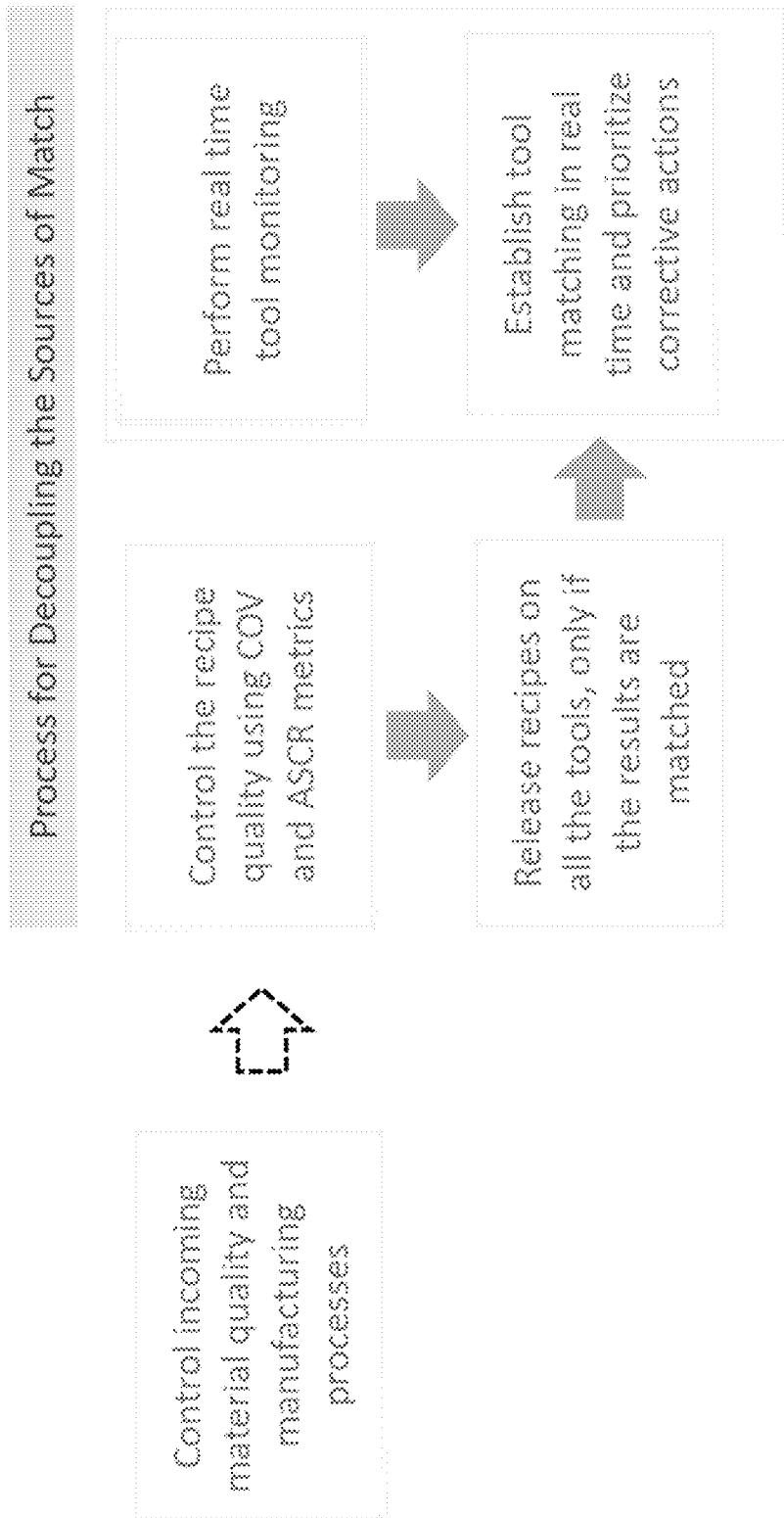
FIG. 23 is another flowchart of an embodiment for decoupling a source of mismatching in accordance with the present disclosure.

While CLI flags a mismatch, it may be unable to identify whether the source of mismatch is hardware or is recipe induced. By controlling the recipe quality through COV and ASCR specs, and testing the recipe for matching prior to its release to production, one can decouple the source of the mismatch captured by the CLI. FIG. 23 describes a process flow decoupling recipe induced and hardware induced tool mismatch. Controlling the recipe can refer to the embodiments related to FIGS. 12, 13, and 19. Releasing recipes on the tools can refer to the embodiments related to FIG. 21. Real time monitoring and establishing tool matching can refer to the embodiments related to FIGS. 1 and 11.

Figure 12:
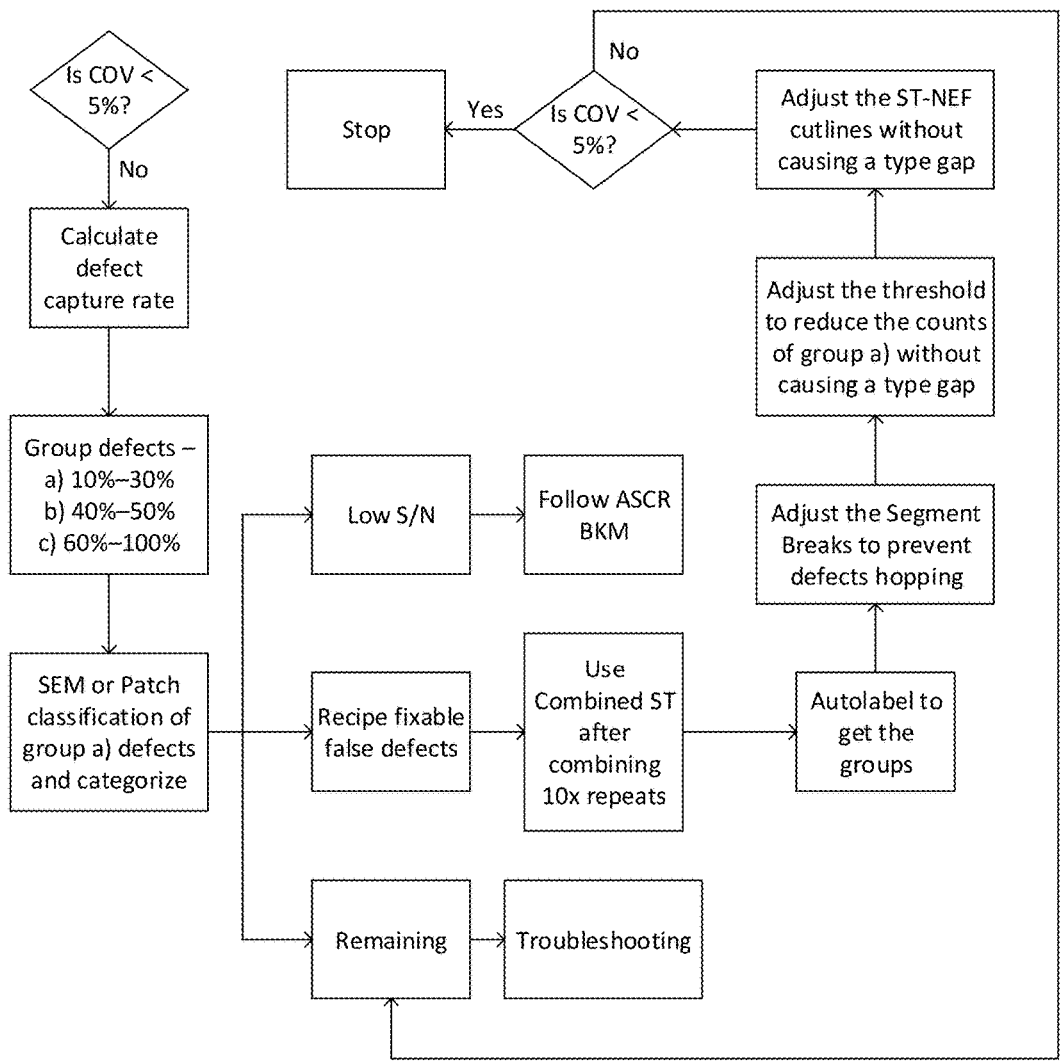
FIG. 12 is a flowchart of an embodiment for reducing COV and increasing ASCR in accordance with the present disclosure.
Figure 13:
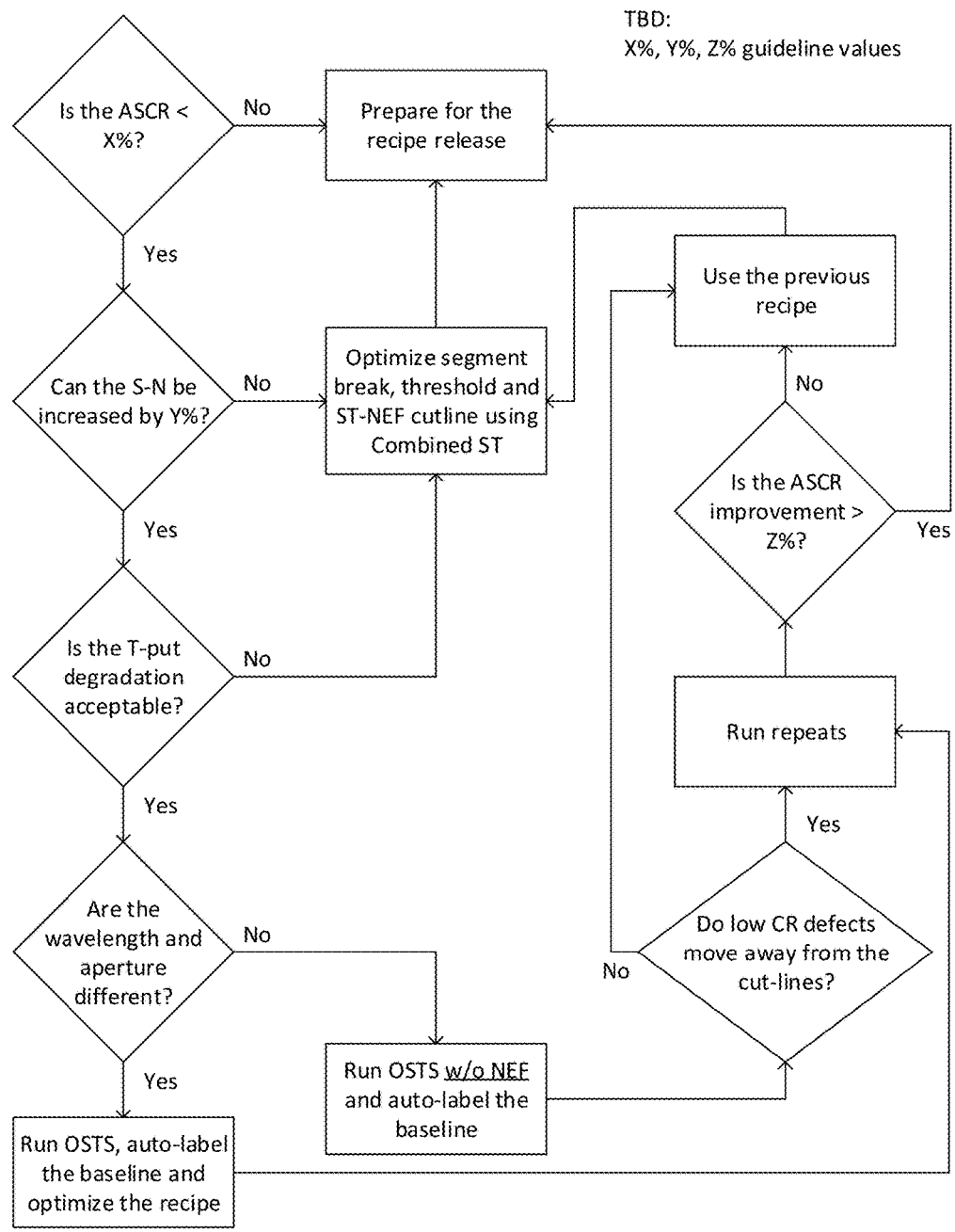
FIG. 13 is another flowchart of an embodiment for reducing COV and increasing ASCR in accordance with the present disclosure.
Figure 14:
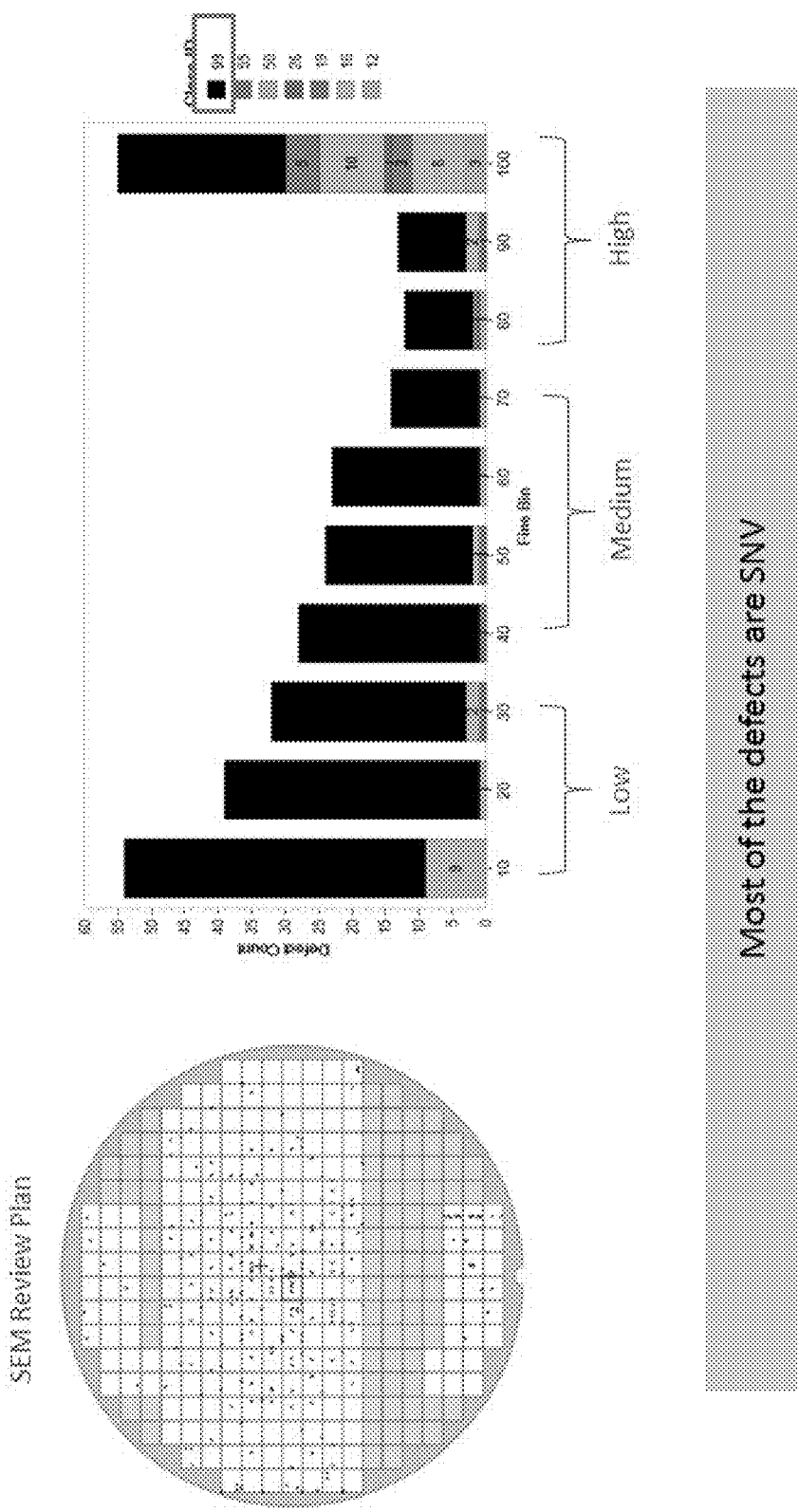
FIGS. 14-16 illustrate the effect of the technique in FIGS. 12-13.
Figure 15:
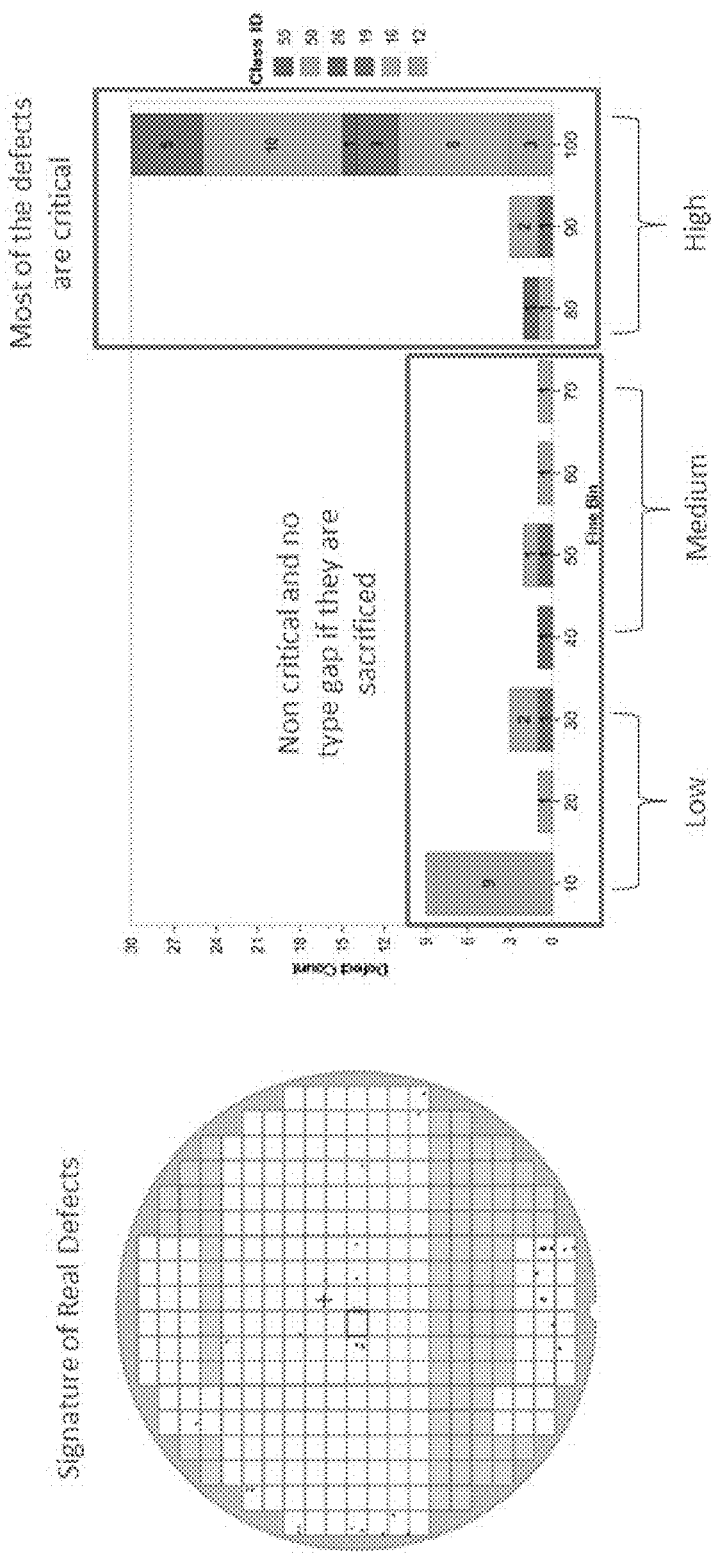
Figure 16:
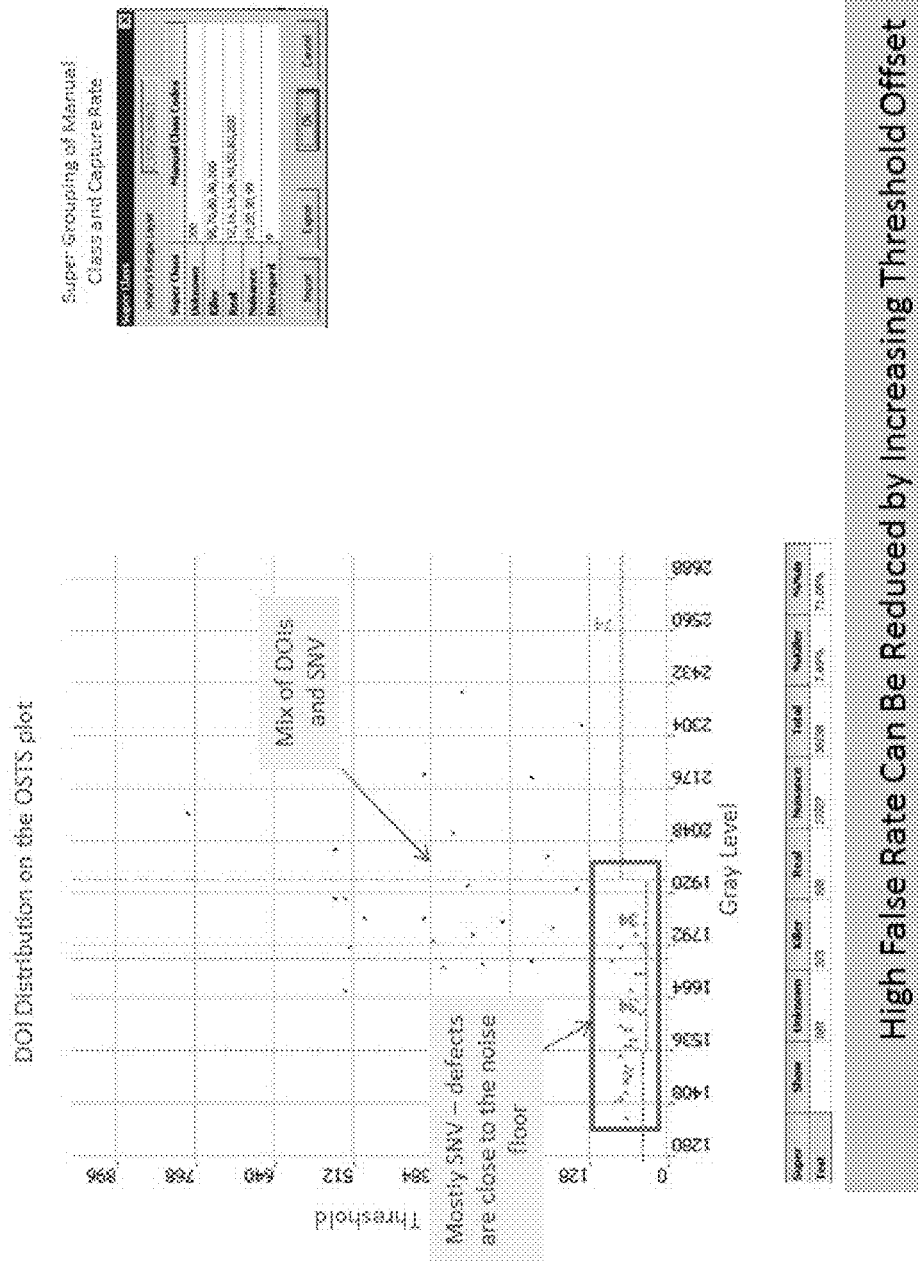

FIGS. 12 and 13 are flowcharts of an embodiment for reducing COV and increasing ASCR. This technique categorizes the low capture rate defects. The process of categorization provides a direction to a user about which problem to solve by which method instead of just using a generic method. For instance, a low capture rate defect because of low signal to noise can be addressed by working on the ways to improve the signal to noise (as shown in FIGS. 14 and 15) in the ASCR methodology. If the low capture rate defects have high signal to noise, then these defects are first treated as a recipe fixable false defects. The user optimizes the recipe to eliminate these defects, with the least trade-off to the sensitivity. If the trade-off cannot be achieved, hardware troubleshooting is done to fix the problem.

An OSTS plot, which is a plot defect count versus defect background gray (or defect segment), is used for recipe optimization to reduce the recipe fixable false defects. Combined results of multiple scans instead of using a single scan result is used for this purpose. The OSTS plot enables the user to identify whether the defects that are low capture rate are close to the tool's noise floor or are becoming low capture rate because they fall in a zone where the background gray level varies run to run or whether it needs some other treatment for suppression. Some other treatment could be a further tuning of ST-NEF or a hardware adjustment. ST-NEF can be assumed to be an add-on recipe component, that classifies the defects into different groups based on their spatial separation and can be used for filtering out undesired defects. For instance, if a defect which is nuisance (like color variation) and has a signal much above the noise floor and it does not fall in a gray level transition area, then the user identifies an attribute that can be effectively used for separating this from another critical defect. The user can set up a new rule to separate this defect and filter out to improve the COV and ASCR. Thus, COV reduction and ASCR improvement are possible.

Figure 17A:
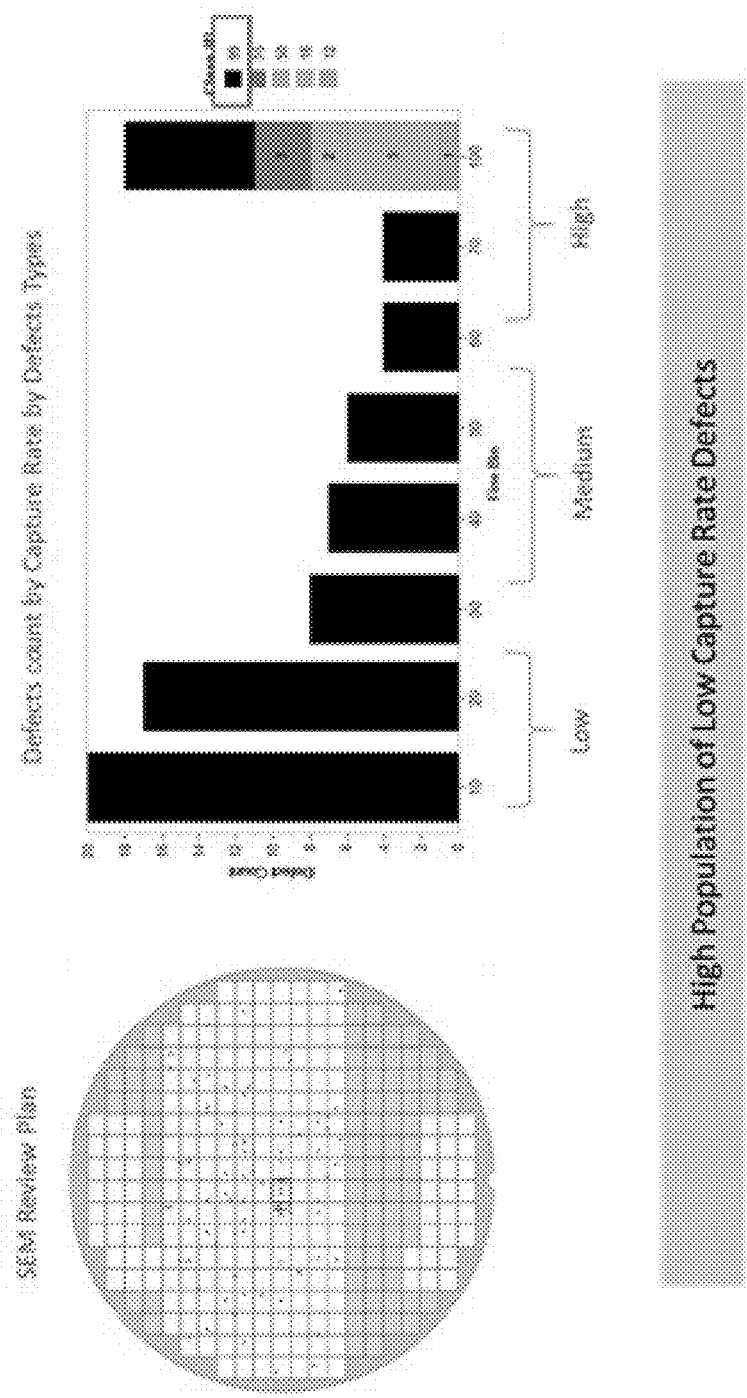
FIGS. 17A-C illustrates an implementation of the technique of FIGS. 12-13.
Figure 17B:
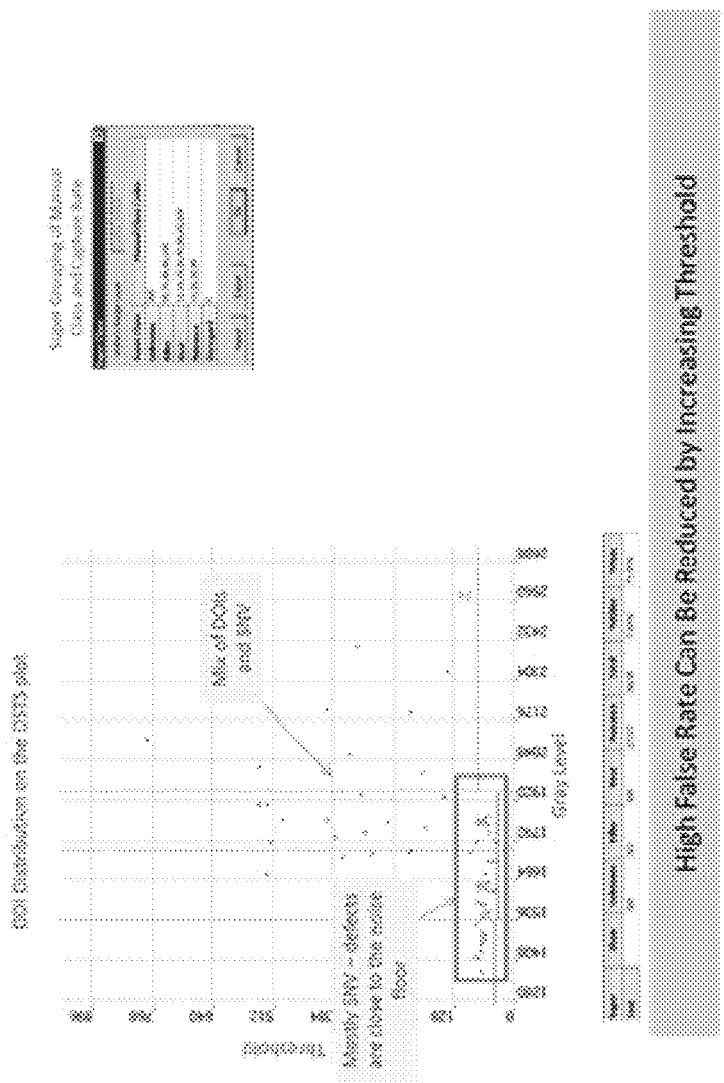
Figure 17C:
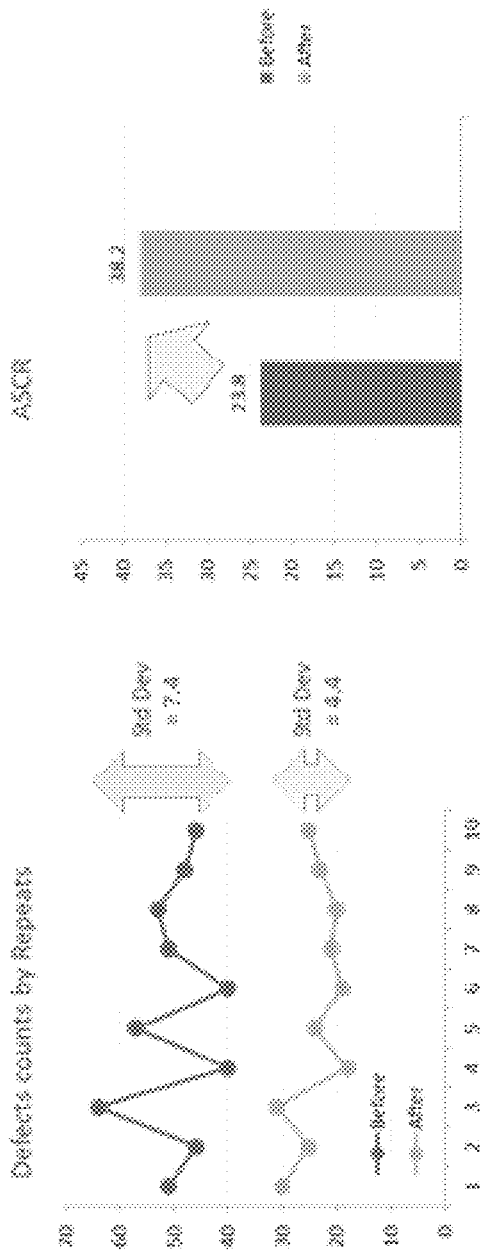

The use of combined results instead of single scan result helps to reduce the limitations of single scan result analysis by compensating for the variations seen in run-to-run. An implementation of the technique shown in FIGS. 14 and 15 is illustrated in FIGS. 17A-C. Low capture rate defects can be categorizes as low signal/noise, recipe fixable false, and the remaining. Combined ST-NEF and OSTS can reduce recipe fixable false and thereby increase ASCR and reduce COV is conceptualized for the first time.

Figure 18:
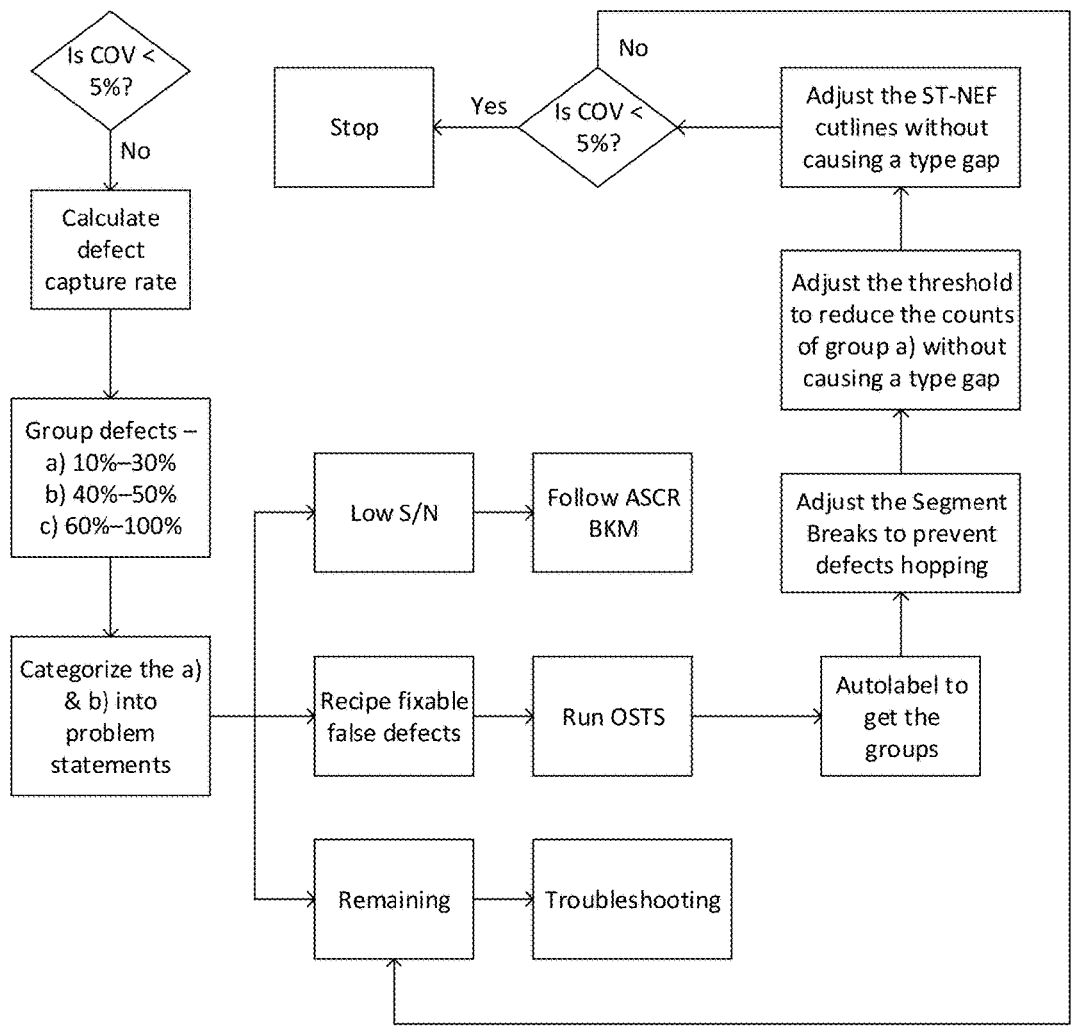
FIG. 18 is another flowchart of an embodiment for reducing COV and increasing ASCR in accordance with the present disclosure.

An alternate technique to reduce COV is shown in the flowchart of FIG. 18.

Figure 19:
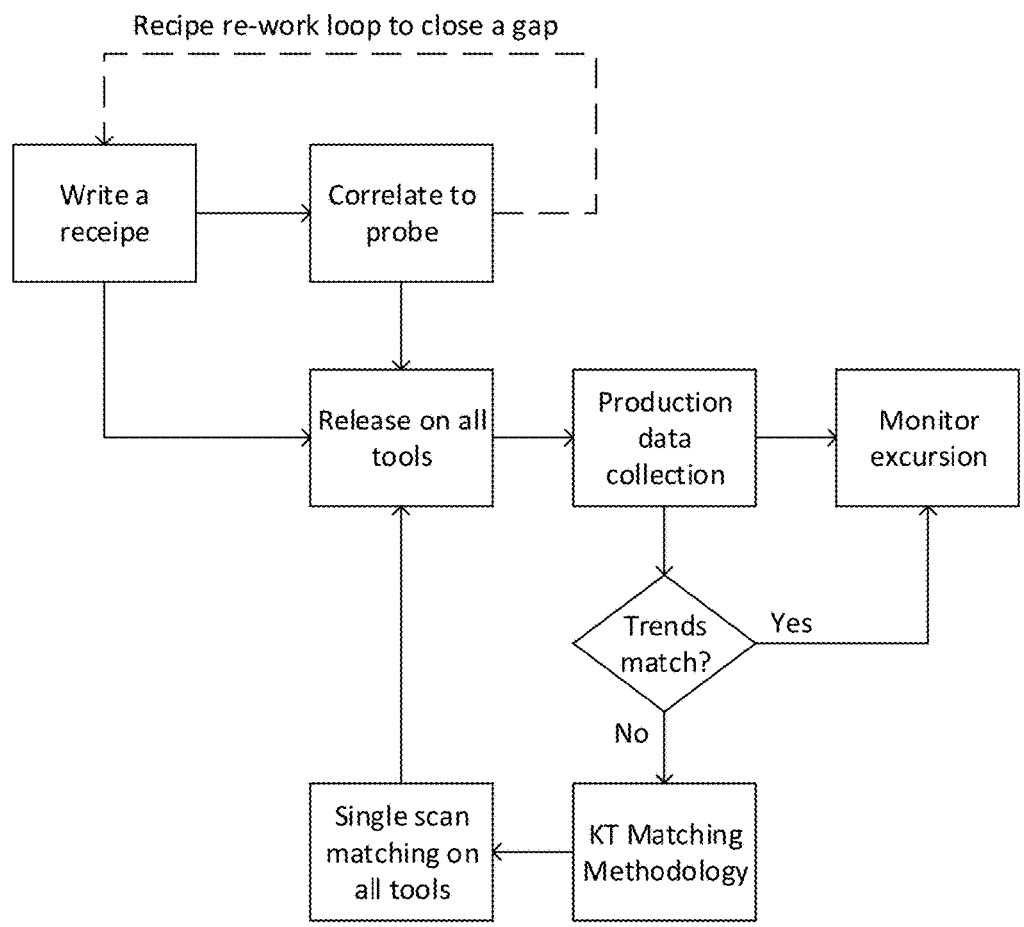
FIGS. 19 and 20 illustrate a recipe release method in accordance with the present disclosure.

FIG. 19 depicts one of the recipe release methods. In this method, the recipe is released to the production as soon as it is ready. This method assumes that the tool has been matched for the hardware states used in the recipe and recipe is robust for production. Consequently, the mismatch gets detected at a later stage and cost of servicing to fix the mismatch increases.

Figure 20:
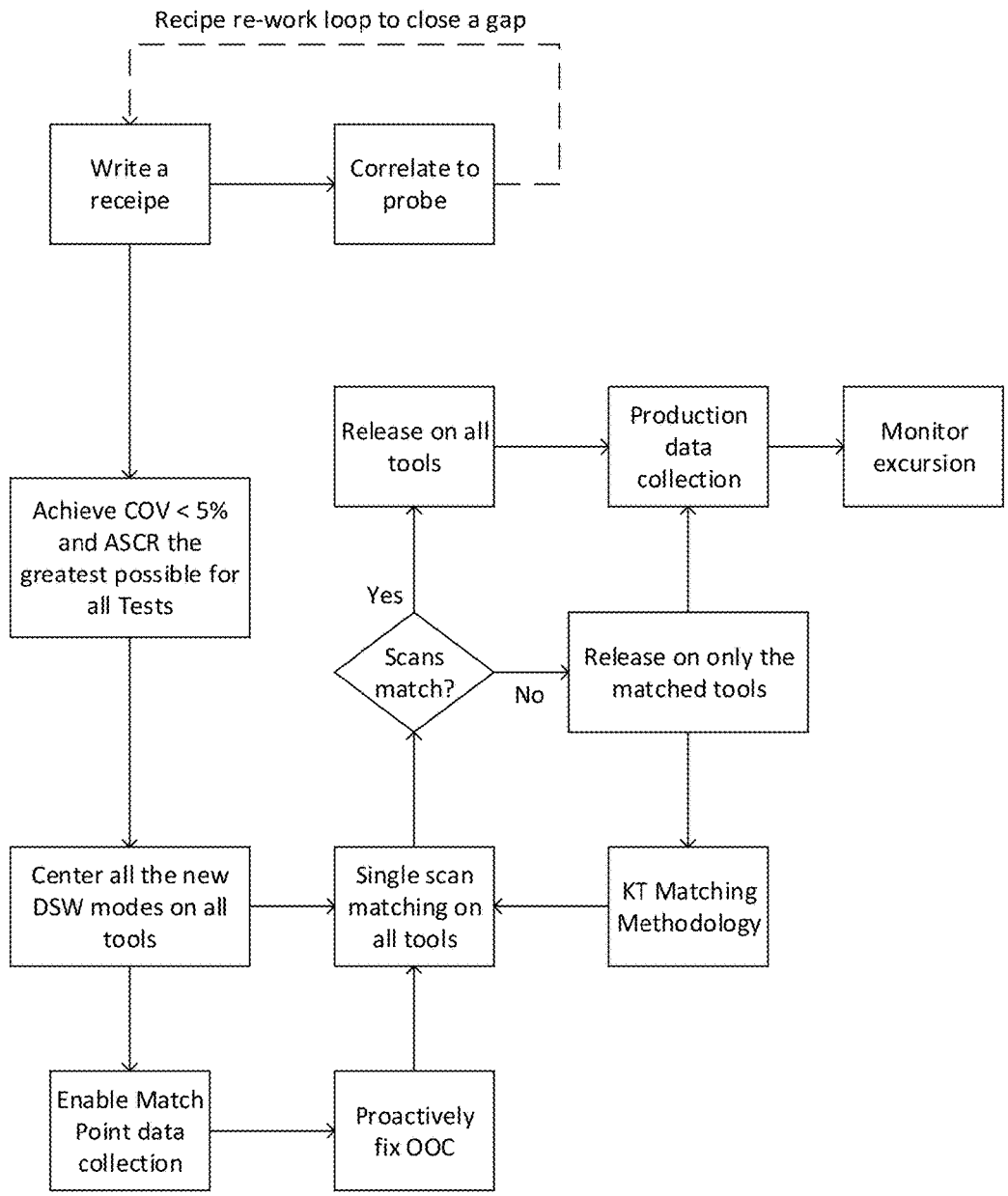

FIG. 20 illustrates an improved recipe release method. This method introduces various checks prior to the recipe release. As shown in the flow chart, the new method proactively attempts to fix the factors, such as COV, ASCR, and hardware matching (DSW mode centering), that are known to cause mismatch. These checks can help reduce the recipe induced mismatch. Use of this technique can ensure that the recipe is stable and robust before it is released to production, can ensure that the tools are calibrated for the states that are used, can ensure that the hardware parameters that were not enabled earlier for real time data collection get added, can proactively look at mismatch before the recipe is released to a fleet of tools, and can provide a mechanism by which the recipe can be released while tool matching is being worked on.

FIG. 21 is a flowchart of an embodiment for tool monitoring and maintenance with real-time data collection. MatchPoint (MP), Klearpoint (KP), Total Uncertainty in Measurement (TMU), CSE Tool Kit, and MP Dashboards, are used. MP pulls the data real time from the tools and stores them in a central database to support MP Dashboard and offline data analysis. TMU is a metric generated using production SPC that indicates whether the tool is mismatched. The MP Dashboard provides a graphical trend of the hardware parameters with their control limits for the data that have been configured for collection.

In the technique of FIG. 21, the MP or CSE kit is used for collecting data. No tool down time is required for this operation. Production SPC data is periodically reviewed to check the TMU score and ensure it is within the acceptable limit. To monitor a tool, a user monitors the MP Dashboard. If any parameter is OOC, necessary corrective action is taken. Otherwise the tool is released to the production. This form of monitoring is supplemented by running a production monitor (PMON). PMON refers to data collection on the tool by inspection of any wafer (standard, monitor, DSW, bare silicon, etc.). PMON is not needed if all the relevant hardware parameters have been configured for data collection. By reducing the number of wafers that are required to be inspected regularly for data collection, tool time availability for the production is improved. Additionally, by collecting the right set of data continuously, the need for a tool downtime to collect data and then troubleshoot is minimized significantly in this scheme of tool release methodology.

The hardware parameters that have an impact on the sensitivity of the tools to catch production issues may be relevant to the production. These can be identified by finding the inspection modes and identifying the hardware parameters whose performance is correlated with these inspection modes. The collection frequency for the data collection can be dependent on the hardware parameter, so it is configured differently for different parameters. This is an improvement over the data collection during PM methodology because PM only targets critical parameters, which may not cover the parameters that affect the production.

When a tool issue occurs, such as being mismatched or having poor performance, the trends of the data of the tool fleet can be checked for the layer (or sample) that was reported. A trend of output from each tool, such as defect count, light level values, histogram, and TMU score, are compared. If there is insignificant deviation in the trend, then the issue may be considered as a false alarm and no action is taken. Otherwise, MP Dashboard may be looked at to check for any OOC. If any hardware parameter is OOC, then it is fixed and the tool can be released. Otherwise, relevant preexisting data (such as DSW lot result or production layer data) can be analyzed to define the problem statement. POAs can be performed to identify the root cause and fix the tool. The hardware parameter that was fixed can be added to the list of parameters that are monitored using MP server.

The hardware parameters that may be relevant to the production can be identified. The MP server can collect these parameters from the tools at a configured frequency. A user can monitors the trend using MP Dashboard and fixes any OOC or drifting trend. When a manufacturer reports a tool issue or mismatch, the user first looks into the MP Dashboard for the trends to identify what to fix. If there are no drifted trends, then POAs are sought for diagnosis and the hardware parameter is added to MP server for data collection.

This technique can reduce or eliminate the need to scan wafer to monitor the tool health through MP server data collection and MP Dashboard. All the parameters relevant to production can be monitored, which can help identify and fix any issue that impact production. Frequent monitoring of the real-time data of the parameters can help to fix the issues faster. This technique also can enable more scheduled PMs and fewer unscheduled PMs.

Figure 22:
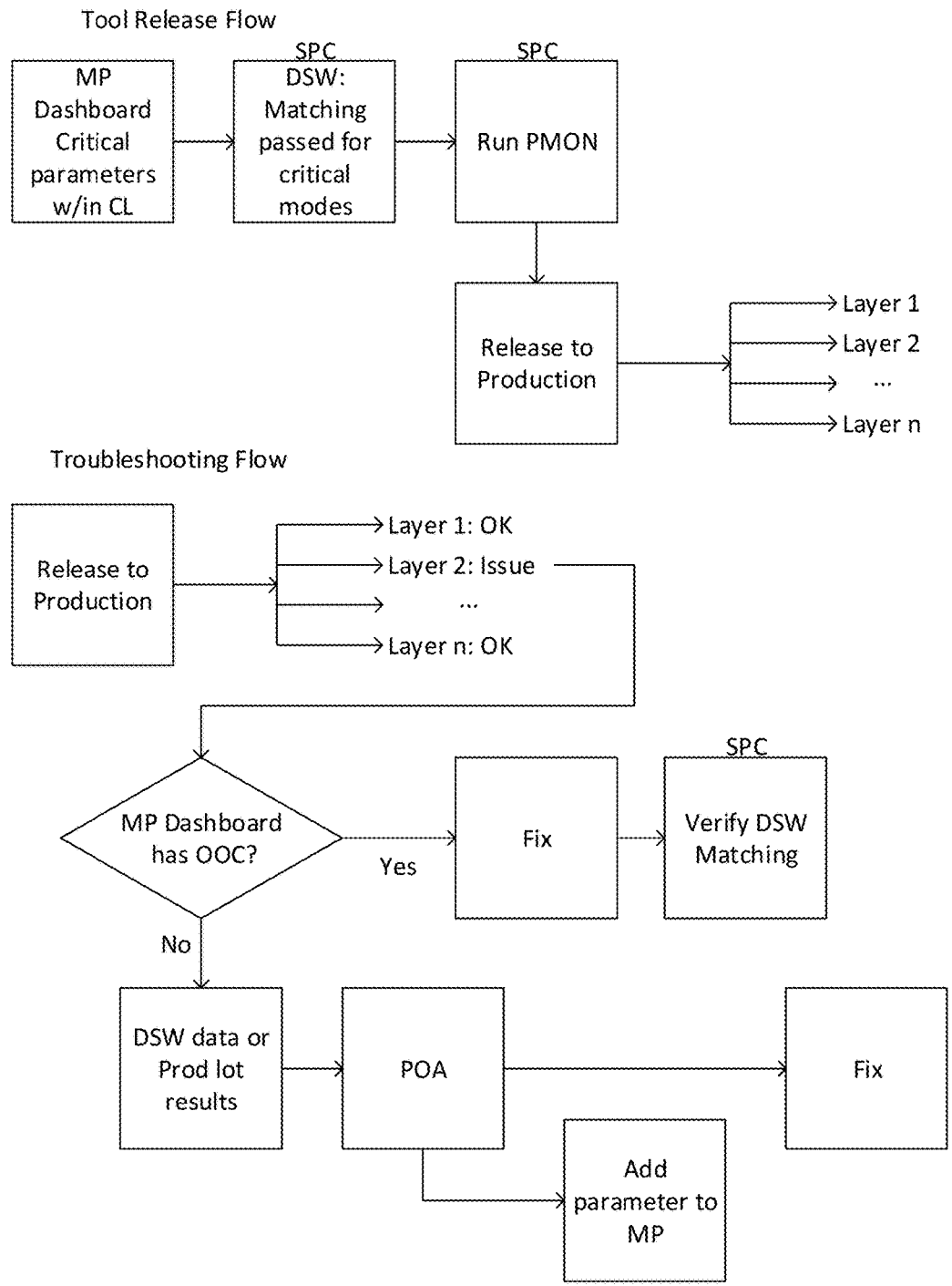
FIG. 22 is another flowchart of an embodiment for tool monitoring and maintenance with real-time data collection in accordance with the present disclosure.

Another flowchart of an embodiment for tool monitoring and maintenance with real-time data collection is shown in FIG. 22.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A system comprising:
an interface in electronic communication with a plurality of semiconductor manufacturing tools; and
a process control unit in electronic communication with the interface, wherein the process control unit is configured to receive production data from the plurality of semiconductor manufacturing tools, wherein the production data include measurements of one or more semiconductor wafers manufactured using the semiconductor manufacturing tools, wherein the production data include parametric data and defect attributes data, wherein the parametric data is of hardware of the plurality of semiconductor manufacturing tools, and wherein the process control unit includes:
a control limit impact (CLI) module that is configured to send an alert if a CLI of the parametric data and the defect attributes data is above a specification;
a defects count identification module that is configured to identify a relationship between a defects count and the parametric data;
a defect attributes identification module that is configured to identify a relationship between at least one trend of the defect attributes data and the parametric data;
a prioritization module that is configured to prioritize causation factors;
a collection module that collects data at different states from the parametric data for two or more of the semiconductor manufacturing tools; and
an image analysis module that is configured to identify one of the states at which the two or more of the semiconductor manufacturing tools match.

2. The system of claim 1, wherein the process control unit includes a processor, an electronic data storage unit in electronic communication with the processor, and a communication port in electronic communication with the processor and the electronic data storage unit.

3. The system of claim 1, wherein the process control unit is programmed to report out-of-control hardware parameters.

4. The system of claim 1, wherein the interface is configured to receive the production data in real-time.

5. The system of claim 1, further comprising a reporting module that is configured to report out-of-control hardware parameters, wherein the out-of-control hardware parameters are determined using the parametric data and the defect attributes data.

6. The system of claim 1, wherein the process control unit is further configured to set a priority for out-of-control hardware parameters based on a CLI score, wherein a higher CLI score corresponds to a higher priority.

7. The system of claim 1, wherein the prioritization module is configured to prioritize the causation factors based on at least one R-square score of the causation factors.

8. The system of claim 1, wherein the image analysis module is programmed to:
convert images to Fast Fourier Transformed (FFT) images;
compare two of the FFT images pixel by pixel to generate a histogram; and
determine an R-square value of results of comparing the two of the FFT images for the histogram, wherein a higher R-square value corresponds to improved matching.

9. The system of claim 1, wherein the image analysis module is programmed to:
define representative structures;
collect image data of the representative structures from two of the semiconductor manufacturing tools; and
determine a value of at least one parameter such that at least some image parameters of the image data match between the two of the semiconductor manufacturing tools.

10. The system of claim 1, wherein the image analysis module is programmed to:
determine at least two optimized hypothesis functions to predict best matching parameters between two of the semiconductor manufacturing tools;
optimize a fitting parameter to minimize mean squared error;
compare the hypothesis function of the two semiconductor manufacturing tools to find an offset vector of an input variable to minimize a difference between two of the hypothesis functions; and
match the two semiconductor manufacturing tools by adjusting tool variables.

11. A method comprising:
receiving, at a process control unit, production data from a plurality of semiconductor manufacturing tools, wherein the production data include measurements of one or more semiconductor wafers manufactured using the semiconductor manufacturing tools, and wherein the production data include parametric data and defect attributes data, wherein the parametric data is of hardware of the plurality of semiconductor manufacturing tools;
determining, using the process control unit, a control limit impact (CLI) of the parametric data and the defect attributes data;
identifying, using the process control unit, a relationship between a defects count and the parametric data;
identifying, using the process control unit, a relationship between at least one trend of the defect attributes data and the parametric data;
prioritizing, using the process control unit, causation factors;
collecting, using the process control unit, the parametric data at different states for two or more of the semiconductor manufacturing tools; and
performing, using the process control unit, image analysis to identify one of the states at which the two or more of the semiconductor manufacturing tools match.

12. The method of claim 11, wherein the production data is received at the process control unit in real-time.

13. The method of claim 11, further comprising reporting out-of-control hardware parameters, wherein the out-of-control hardware parameters are determined using the parametric data and the defect attributes data.

14. The method of claim 11, further comprising setting a priority for out-of-control hardware parameters based on a CLI score, wherein a higher CLI score corresponds to a higher priority.

15. The method of claim 11, further comprising monitoring the parametric data against a control limit, wherein the control limit is defined based on manufacturing specifications or based on sigma limits.

16. The method of claim 11, wherein the CLI is measured to determine a mismatch between at least two of the semiconductor manufacturing tools.

17. The method of claim 16, wherein a correlation between a random defect count and the parametric data is performed.

18. The method of claim 11, wherein the prioritizing is based on at least one R-square score of the causation factors.

19. The method of claim 18, wherein the R-square score for each of the causation factors is ranked.

20. The method of claim 11, wherein the image analysis includes:
   converting images to Fast Fourier Transformed (FFT) images;
   comparing two of the FFT images pixel by pixel to generate a histogram; and
   determining an R-square value of results of comparing the two of the FFT images for the histogram, wherein a higher R-square value corresponds to improved matching.

21. The method of claim 11, wherein the image analysis includes:
   defining representative structures;
   collecting image data of the representative structures from two of the semiconductor manufacturing tools; and
   determining a value of at least one parameter such that at least some image parameters of the image data match between the two of the semiconductor manufacturing tools.

22. The method of claim 11, wherein the image analysis includes:
   determining at least two optimized hypothesis functions to predict best matching parameters between two of the semiconductor manufacturing tools;
   optimizing a fitting parameter to minimize mean squared error;
   comparing the hypothesis function of the two semiconductor manufacturing tools to find an offset vector of an input variable to minimize a difference between two of the hypothesis functions; and
   matching the two semiconductor manufacturing tools by adjusting tool variables.

23. The method of claim 22, further comprising:
   randomly selecting a first percentage of defects as a learning set, a second percentage of defects as a cross-validation set, and remainder percentage as a test set; and
   testing the hypothesis functions using the cross-validation set.

* * * * *